United States Patent
Minami et al.

(10) Patent No.: US 8,557,194 B2
(45) Date of Patent: Oct. 15, 2013

(54) CARRIER, PROCESS FOR PRODUCING SAME, BIOREACTOR, AND CHIP FOR SURFACE PLASMON RESONANCE ANALYSIS

(75) Inventors: Koichi Minami, Ashigarakami-gun (JP); Yohsuke Takeuchi, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 13/188,637

(22) Filed: Jul. 22, 2011

(65) Prior Publication Data
US 2011/0274846 A1 Nov. 10, 2011

Related U.S. Application Data

(62) Division of application No. 12/171,751, filed on Jul. 11, 2008, now abandoned.

(30) Foreign Application Priority Data

| Jul. 13, 2007 | (JP) | 2007-184675 |
| Jul. 13, 2007 | (JP) | 2007-184676 |
| Mar. 10, 2008 | (JP) | 2007-059221 |
| Mar. 12, 2008 | (JP) | 2008-062921 |

(51) Int. Cl.
*B05D 5/00* (2006.01)
*B05D 1/36* (2006.01)

(52) U.S. Cl.
USPC .......................... 422/400; 422/62

(58) Field of Classification Search
USPC ................................ 422/57, 400, 62
See application file for complete search history.

(56) References Cited

U.S. PATENT DOCUMENTS

| 5,242,828 A * | 9/1993 | Bergstrom et al. ........ 435/287.1 |
| 5,439,829 A | 8/1995 | Anderson et al. |
| 5,620,850 A | 4/1997 | Bamdad et al. |
| 5,624,537 A | 4/1997 | Turner et al. |
| 6,322,979 B1 * | 11/2001 | Bamdad et al. ............. 435/6.12 |

(Continued)

FOREIGN PATENT DOCUMENTS

| EP | 1 541 234 A1 | 6/2005 |
| JP | 10-505910 A | 6/1998 |

(Continued)

OTHER PUBLICATIONS

Frutos, A.G.; Brockman, J.M.; Corn, R.M. "Reversible Protection and Reactive Patterning of Amine and Hydroxyl-Terminated Self-Assembled Monolayers on Gold Surfaces for the Fabrication of Biopolymer Arrays," Langmuir, 2000, 16, pp. 2192-2197.*

(Continued)

*Primary Examiner* — Christine T Mui
(74) *Attorney, Agent, or Firm* — Sughrue Mion, PLLC

(57) ABSTRACT

A carrier comprises a base plate, a polymeric film, which has been bound on a surface of the base plate, and a ligand, which has been bound with the polymeric film. The ligand has been bound with the polymeric film at a density falling within the range of $1.0 \times 10^{16}$ pieces/mm$^3$ to $3.3 \times 10^{18}$ pieces/mm$^3$. The carrier is produced with a process, comprising the steps of: causing the polymeric film to bind on the base plate, and causing the ligand to bind with the polymeric film, the step of causing the ligand to bind with the polymeric film being performed in an organic solvent.

7 Claims, 4 Drawing Sheets

(56) References Cited

U.S. PATENT DOCUMENTS

| | | | |
|---|---|---|---|
| 7,179,660 B1* | 2/2007 | Kirakossian et al. | 436/529 |
| 7,745,608 B2* | 6/2010 | Manoharan et al. | 536/24.5 |
| 8,071,177 B2* | 12/2011 | Minami | 427/419.1 |
| 2003/0218130 A1 | 11/2003 | Boschetti et al. | |
| 2004/0091874 A1 | 5/2004 | Yamasaki et al. | |
| 2006/0040274 A1 | 2/2006 | Tsinberg | |
| 2007/0099840 A1* | 5/2007 | Ulijn et al. | 514/17 |
| 2007/0111353 A1 | 5/2007 | McCaskill et al. | |
| 2008/0044925 A1 | 2/2008 | Isojima et al. | |
| 2010/0022730 A1* | 1/2010 | Hatakeyama et al. | 526/246 |

FOREIGN PATENT DOCUMENTS

| | | | |
|---|---|---|---|
| JP | 2002-062297 A | | 2/2002 |
| JP | 2003-344404 A | | 12/2003 |
| JP | 2004-125461 A | | 4/2004 |
| JP | 2005-526972 A | | 9/2005 |
| JP | 2006-266831 A | | 10/2006 |
| WO | 96/09547 A2 | | 3/1996 |
| WO | WO 9811919 A2 | * | 3/1998 |
| WO | 00/47548 A1 | | 8/2000 |
| WO | 03/000708 A1 | | 1/2003 |
| WO | 2005/120700 A2 | | 6/2005 |
| WO | 2006/038456 A1 | | 4/2006 |

OTHER PUBLICATIONS

Rich et al, "Kinetic analysis of estrogen receptor ligand interactions," PNAS, 2002, 99, pp. 8562-8567.*

Lofas, "Dextran modified self-assembled monolayer surfaces for use in biointeraction analysis with surface plasmon resonance," Pure & Appl. Chem., 1995, vol. 67, No. 5, pp. 829-834.*

Definition of base: sodium phosphate. download date Jul. 29, 2012. 3 pages.*

GE Healthcare Biacore Sensor Surface Handbook. Feb. 2005. 100 pages.*

Biacore Sensor Surface Handbook. Oct. 2003. 112 pages.*

Khan et al., "Double-Hexahistidine Tag with High-Affinity Binding for Protein Immobilization, Purification, and Detection on Ni-Nitrilotriacetic Acid Surfaces and Detection on Ni-Nitrilotriacetic Acid Surfaces," Analytical Chemistry, 2006, vol. 78, No. 9, pp. 3072-3079.

Lata et al., "Stable and Functional Immobilization of Histidine-Tagged Proteins via Multivalent Chelator Headgroups on a Molecular Poly(ethylene glycol) Brush," Analytical Chemistry, 2005, vol. 77, No. 4, pp. 1096-1105.

Camperi, S.A., "Preparation and Characterisation of Immobilised Metal ion Hollow-Fibre Polysulphone Membranes. Their Application in High-Speed Pectic Enzyme Fractionation," Process Biochemistry, 2004, vol. 39, pp. 1017-1024.

Camperi et al., "High-Speed Pectic Enzyme Fractionation by Immobilized Metal Ion Affinite Membranes," Bioseparation, 2000, vol. 9, pp. 173-177.

Suen et al., "Exploiting Immobilized Metal Affinity Membranes for the Isolation or Purification of Therapeutically Relevant Species," J. of Chromatography B, 2003, vol. 797, pp. 305-319.

European Patent Office Communication in EP No. 08 012 501.6, dated Apr. 11, 2011.

Liedberg et al., "Biosensing with Surface Plasmon Resonance—How It All Started," Biosensors & Bioelectronics, 1995, vol. 10, pp. i-ix.

Bamdad, C., "The Use of Variable Density Self-Assembled Monolayers to Probe the Structure of a Target Molecule," Biophysical Journal, 1998, vol. 75, pp. 1989-1996.

Lori et al., "Development and Characterization of Nickel-NTA-Polyaniline Modified Electrodes," Electroanalysis, 2006, vol. 18, No. 1, pp. 77-81.

Japanese Patent Office, Office Action issued in corresponding JP Application No. 2008-059221, dated Dec. 6, 2011.

Japanese Patent Office, Office Action issued in corresponding JP Application No. 2008-062921, dated Nov. 29, 2011.

Japanese Patent Office, Office Action issued in corresponding JP Application No. 2008-059221, dated Apr. 3, 2012.

* cited by examiner

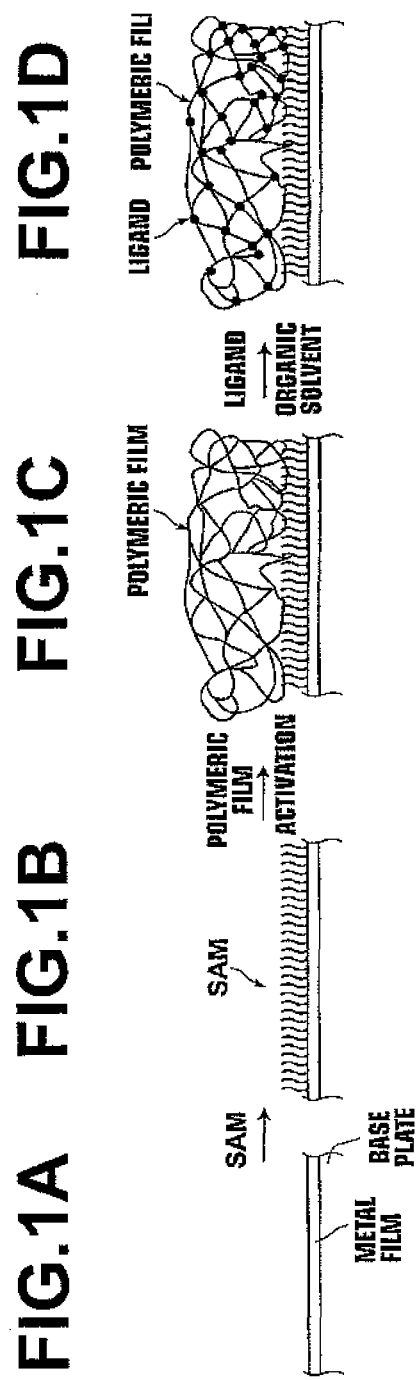

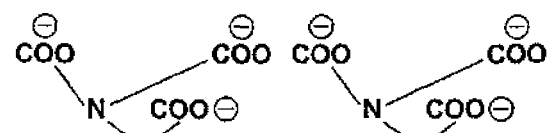
FIG.2A
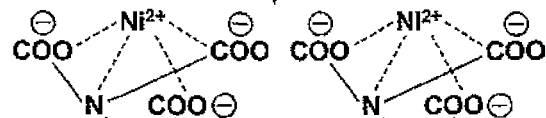
FIG.2B
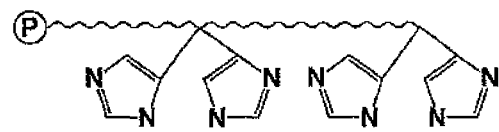
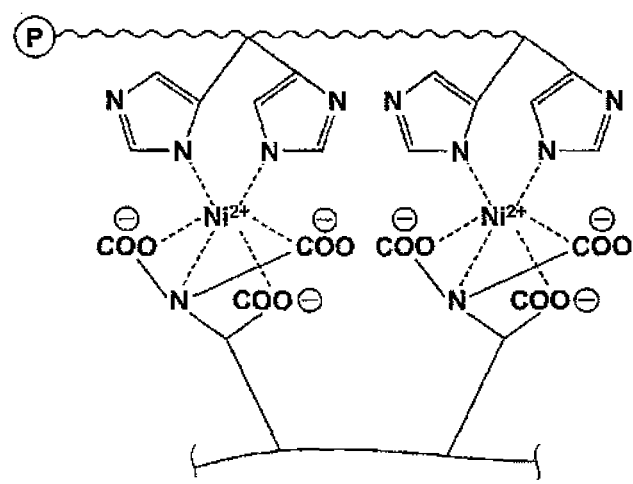
FIG.2C

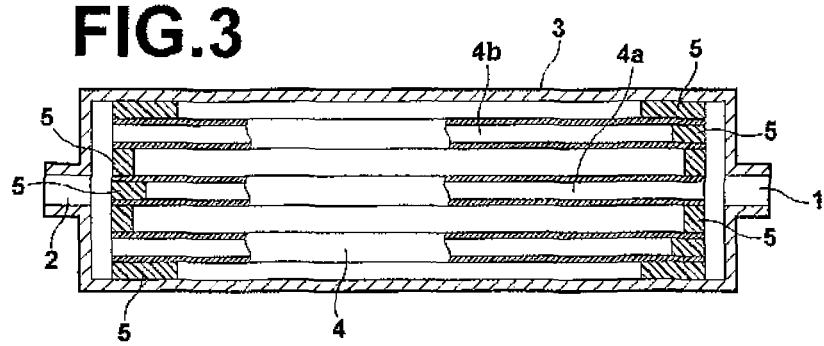
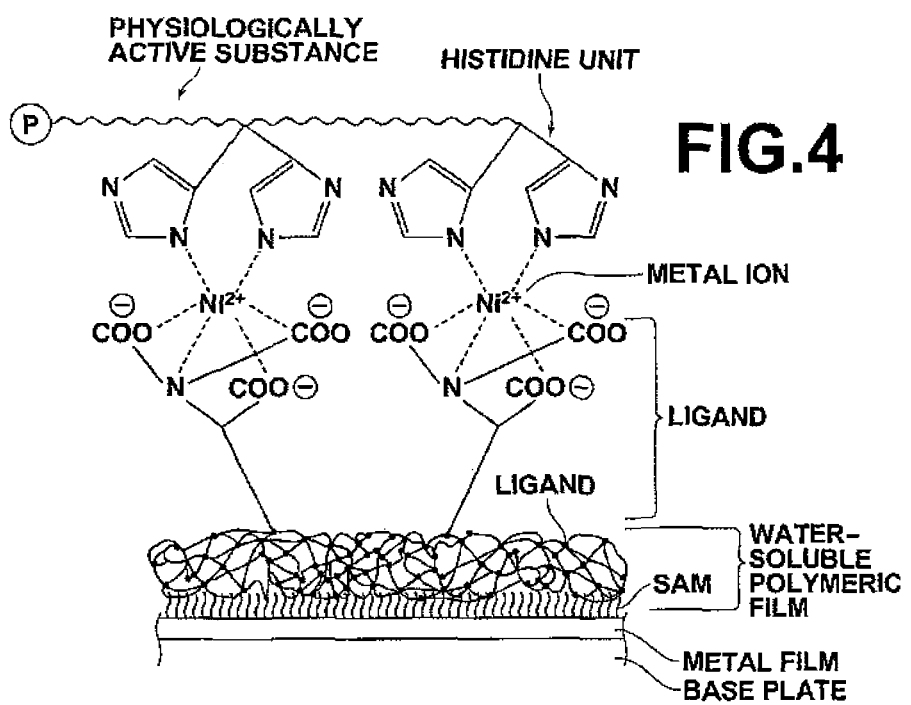

CARRIER, PROCESS FOR PRODUCING SAME, BIOREACTOR, AND CHIP FOR SURFACE PLASMON RESONANCE ANALYSIS

CROSS-REFERENCE TO RELATED APPLICATIONS

This is a divisional of application Ser. No. 12/171,751 filed Jul. 11, 2008, claiming priority based on Japanese Patent Application No. 184675/2007 filed Jul. 13, 2007, Japanese Patent Application No. 184676/2007 filed Jul. 13, 2007, Japanese Patent Application No. 059221/2008 filed Mar. 10, 2008, and Japanese Patent Application No. 062921/2008 filed Mar. 12, 2008, the contents of all of which are incorporated herein by reference in their entirety.

BACKGROUND OF THE INVENTION

1. Field of the Invention

This invention relates to a carrier adapted for fixation of a physiologically active substance, and a process for producing the carrier. This invention also relates to a bioreactor comprising the carrier. This invention further relates to a chip for surface plasmon resonance analysis.

2. Description of the Related Art

Various analyses utilizing intermolecular interactions, such as immune reactions, have heretofore been performed in the fields of clinical examinations, and the like. Among others, several kinds of techniques, which do not require complicated operations and labeling substances and which are capable of detecting alterations in binding quantities of analyzed substances with a high sensitivity, have heretofore been used. Examples of the techniques described above include surface plasmon resonance (SPR) analysis techniques, quartz crystal oscillator microbalance (QCM) analysis techniques, and analysis techniques utilizing functional surfaces, such as surfaces of gold colloidal particles and ultrafine particles. In each of the techniques described above, a surface for fixation of a physiologically active substance is important. By way of example, the surface plasmon resonance (SPR) analysis techniques will be described hereinbelow.

Ordinarily, an analysis chip for use in analysis of a physiologically active substance is provided with a transparent base plate (e.g., a glass plate), a metal film, which has been formed on the transparent base plate by use of a vacuum evaporation processing, and a thin film, which has been formed on the metal film and which has a functional group capable of fixing a physiologically active substance, such as a protein. The physiologically active substance is fixed to the metal surface via the functional group. A specific binding reaction between the physiologically active substance and a sample substance is analyzed, and an interaction between biomolecules is thereby analyzed.

There have been known several techniques for fixation of a physiologically active substance to an analysis chip. For example, in cases where the physiologically active substance is a protein, as a technique for fixing the analysis chip and the protein with each other through covalent bonding, there has been known a technique (i.e., an amine coupling technique), wherein an amino group of the protein and a carboxyl group on the analysis chip are bound with each other. However, with the amine coupling technique, since an arbitrary amino group on the surface of the protein is modified due to the fixation, it often occurs that the orientation of fixed protein is not capable of coinciding with a predetermined orientation, or it often occurs that the binding of the protein and the substrate with each other is obstructed by the position of the modified amino group, and that the activity of the protein becomes low. Also, with the amine coupling technique, it is necessary for the protein to be concentrated on the analysis chip, and it is necessary that, at the time of the fixation, the protein is dissolved in a buffer solution, which has a pH value lower than pI of the protein to be fixed and which has a low ionic strength. Therefore, in the cases of a protein which undergoes denaturation under the conditions described above, the problems occur in that the fixation of the protein is not capable of being performed with the activity of the protein being kept.

Also, there have been developed techniques, wherein a protein is fixed onto an analysis chip under neutral conditions by use of a part referred to as a tag, which has been introduced to an N terminal or a C terminal of a protein having been synthesized artificially through generic alteration. A typical example of the technique described above is a fixation technique utilizing His-tag. The fixation technique utilizing the His-tag has been developed for an affinity column for purification of a His-tag protein having been expressed through genetic recombination. The fixation technique utilizing the His-tag has also been used for fixing a protein onto a solid surface such that the protein may have predetermined orientational characteristics.

Particularly, with a technique for fixation of the His-tag protein, wherein an NTA-Ni(II) complex having been formed from nitrilotriacetic acid (NTA) and an Ni(II) ion is utilized, water molecules having coordinated with two coordinating dentations in the complex are substituted by nitrogen atoms of two imidazole groups of an oligohistidine residue of the His-tag protein, and the His-tag protein is thereby bound with the solid surface specifically and in a predetermined direction. With the technique for fixation of the His-tag protein, wherein the NTA-Ni(II) complex is utilized, since pre-concentration under acidic conditions need not be performed, the fixation of the His-tag protein by use of a buffer solution (such as PBS) under physiological conditions is capable of being performed, and the problems encountered with the amine coupling technique are capable of being eliminated.

However, since the combination of the His-tag protein and the NTA-Ni(II) complex with each other has been developed for the purposes of the purification with the affinity column, the binding between the His-tag protein and the NTA-Ni(II) complex is not sufficiently strong, and the problems with regard to dissociation equilibrium are encountered. Therefore, the problems occur in that the His-tag protein having been fixed via the NTA-Ni(II) complex onto the analysis chip undergoes dissociation little by little from the analysis chip. Accordingly, the combination of the His-tag protein and the NTA-Ni(II) complex with each other is not capable of being applied directly to the use applications for biosensors, and the like.

Several studies have been made for solving the problems with regard to the dissociation described above. For example, fixation techniques, wherein substitution inactivation of a metal ion coordinating with the His-tag protein is effected through oxidation with an oxidizing agent, or the like, are disclosed in Japanese Unexamined Patent Publication No. 2006-266831 and U.S. Pat. No. 5,439,829 corresponding to Japanese Unexamined Patent Publication No. 6(1994)-157600. However, with the disclosed fixation techniques, the problems often occur, depending upon the oxidation rate and the kind of the oxidizing agent, in that deactivation of the protein arises. Also, an attempt for improving the binding by the utilization of triNTA, in lieu of NTA described above, as a ligand is described in, for example, International Patent Publication No. WO00/047548. However, with the attempt for improving the binding by the utilization of triNTA, it is not always possible to obtain practically sufficient fixation.

A technique for fixing NTA to a polysaccharide is disclosed in, for example, Farid Khan et al., "Double-Hexahistidine Tag with High-Affinity Binding for Protein Immobilization, Purification, and Detection on Ni-Nitrilotriacetic Acid Surfaces", Analytical Chemistry, Vol. 78, No. 9, pp. 3072-3079, 2006. Also, a technique for fixation of the His-tag protein utilizing the NTA-Ni(II) complex, wherein the imidazole groups of the His-tag protein and NI(II) are bound at multiple points with the NTA ligand, is disclosed in, for example, Suman Late and Jacob Piehler, "Stable and Functional Immobilization of Histidine-Tagged Proteins via Multivalent Chelator Headgroups on a Molecular Poly(ethylene glycol) Brush", Analytical Chemistry, Vol. 77, No. 4, pp. 1096-1105, 2005.

It may be presumed that, in cases where the physiologically active substance is capable of being supported at multiple points, the binding force will be capable of being enhanced, and the aforesaid problems with regard to the dissociation will be capable of being solved. However, in Farid Khan et al., "Double-Hexahistidine Tag with High-Affinity Binding for Protein Immobilization, Purification, and Detection on Ni-Nitrilotriacetic Acid Surfaces", Analytical Chemistry, Vol. 78, No. 9, pp. 3072-3079, 2006, and Suman Lata and Jacob Piehler, "Stable and Functional Immobilization of Histidine-Tagged Proteins via Multivalent Chelator Headgroups on a Molecular Poly(ethylene glycol) Brush", Analytical Chemistry, Vol. 77, No. 4, pp. 1096-1105, 2005, nothing is studied with respect to a level of an NTA density, with which the problems with regard to the dissociation will be capable of being solved. Also, with the fixation technique described in Suman Late and Jacob Piehler, "Stable and Functional Immobilization of Histidine-Tagged Proteins via Multivalent Chelator Headgroups on a Molecular Poly(ethylene glycol) Brush", Analytical Chemistry, Vol. 77, No. 4, pp. 1096-1105, 2005, since the ligands close to each other are rigid and are not capable of moving flexibly, the problems are encountered in that the metal is not always capable of coordinating at multiple points with the protein, and in that actually it is not always possible to fix the protein reliably at multiple points.

SUMMARY OF THE INVENTION

The primary object of the present invention is to provide a carrier, which is capable of reliably fixing a physiologically active substance.

Another object of the present invention is to provide a process for producing the carrier.

A further object of the present invention is to provide a bioreactor comprising the carrier.

A still further object of the present invention is to provide a chip for surface plasmon resonance analysis.

The present invention provides a carrier, comprising:
i) a base plate,
ii) a polymeric film, which has been bound on a surface of the base plate, and
iii) a ligand, which has been bound with the polymeric film,
the ligand having been bound with the polymeric film at a density falling within the range of $1.0 \times 10^{16}$ pieces/mm$^3$ to $3.3 \times 10^{18}$ pieces/mm$^3$.

The carrier in accordance with the present invention should preferably be modified such that the ligand is a nitrilotriacetic acid derivative.

Also, the carrier in accordance with the present invention should preferably be modified such that a metal ion has been fixed to the ligand.

Further, the carrier in accordance with the present invention should preferably be modified such that a physiologically active substance has been fixed to the metal ion. Furthermore, the carrier in accordance with the present invention should preferably be modified such that the metal ion is a transition metal ion.

Also, the carrier in accordance with the present invention should preferably be modified such that the physiologically active substance has a functional group, which is capable of coordinating with the transition metal ion, and
the physiologically active substance has been fixed by the functional group to the transition metal ion.

Further, the carrier in accordance with the present invention should preferably be modified such that the functional group is an imidazole group.

Furthermore, the carrier in accordance with the present invention should preferably be modified such that the polymeric film has been bound on the surface of the base plate via a self-assembled monolayer. Also, the carrier in accordance with the present invention should preferably be modified such that the polymeric film is a hydrophilic polymer.

The present invention also provides a process for producing a carrier, comprising the steps of:
i) causing the polymeric film to bind on the base plate, and
ii) causing the ligand to bind with the polymeric film,
the step of causing the ligand to bind with the polymeric film being performed in an organic solvent.

The process for producing a carrier in accordance with the present invention should preferably be modified such that the organic solvent is an aprotic type polar solvent. In such cases, the aprotic type polar solvent should more preferably be selected from the group consisting of dimethyl sulfoxide (DMSO) and N,N-dimethylformamide (DMF).

The carrier in accordance with the present invention is capable of being utilized appropriately as a carrier for a bioreactor or a biosensor.

The present invention further provides a chip for surface plasmon resonance analysis, comprising:
i) a sensor chip base plate,
ii) a metal film, which has been located on a surface of the sensor chip base plate,
iii) a water-soluble polymeric film, which has been bound with the metal film,
iv) a ligand, which has been bound with the water-soluble polymeric film,
v) a metal ion, which has coordinated with the ligand, and
vi) a physiologically active substance, which has been fixed to the metal ion,
the ligand having been bound with the water-soluble polymeric film at a density falling within the range of $1.0 \times 10^{16}$ pieces/mm$^3$ to $3.3 \times 10^{18}$ pieces/mm$^3$,
the physiologically active substance having at least seven histidine units, each of which is capable of coordinating with the metal ion,
the physiologically active substance having been fixed to the metal ion via each of the histidine units.

The chip for surface plasmon resonance analysis in accordance with the present invention should preferably be modified such that the physiologically active substance has at least eight histidine units.

Also, the chip for surface plasmon resonance analysis in accordance with the present invention should preferably be modified such that the ligand is nitrilotriacetic acid (NTA).

Further, the chip for surface plasmon resonance analysis in accordance with the present invention should preferably be modified such that the water-soluble polymeric film is constituted of carboxy-modified dextran.

Furthermore, the chip for surface plasmon resonance analysis in accordance with the present invention should preferably be modified such that the metal film is constituted of at least one kind of metal selected from the group consisting of gold, silver, copper, platinum, palladium, and aluminum.

The carrier in accordance with the present invention comprises:
   i) the base plate,
   ii) the polymeric film, which has been bound on the surface of the base plate, and
   iii) the ligand, which has been bound with the polymeric film,
the ligand having been bound with the polymeric film at a density falling within the range of $1.0\times10^{16}$ pieces/mm$^3$ to $3.3\times10^{8}$ pieces/mm$^3$.

Therefore, with the carrier in accordance with the present invention, the physiologically active substance is capable of being fixed by the ligand at multiple points. Accordingly, the physiologically active substance is capable of being fixed reliably.

The process for producing a carrier in accordance with the present invention comprises the steps of:
   i) causing the polymeric film to bind on the base plate, and
   ii) causing the ligand to bind with the polymeric film,
the step of causing the ligand to bind with the polymeric film being performed in the organic solvent.

Therefore, with the process for producing a carrier in accordance with the present invention, the ligand is capable of being bound at a high density with the polymeric film.

The chip for surface plasmon resonance analysis in accordance with the present invention comprises:
   i) the sensor chip base plate,
   ii) the metal film, which has been located on the surface of the sensor chip base plate,
   iii) the water-soluble polymeric film, which has been bound with the metal film,
   iv) the ligand, which has been bound with the water-soluble polymeric film,
   v) the metal ion, which has coordinated with the ligand, and
   vi) the physiologically active substance, which has been fixed to the metal ion,
the ligand having been bound with the water-soluble polymeric film at a density falling within the range of $1.0\times10^{16}$ pieces/mm$^3$ to $3.3\times10^{18}$ pieces/mm$^3$,
the physiologically active substance having at least seven histidine units, each of which is capable of coordinating with the metal ion,
the physiologically active substance having been fixed to the metal ion via each of the histidine units.

Therefore, with the chip for surface plasmon resonance analysis in accordance with the present invention, the fixation of each of the histidine units, which the physiologically active substance has, and the metal ion with each other and the fixation of the metal ion and the ligand with each other are capable of being performed at multiple points. Accordingly, the physiologically active substance is capable of being fixed reliably.

The present invention will hereinbelow be described in further detail with reference to the accompanying drawings.

BRIEF DESCRIPTION OF THE DRAWINGS

FIGS. 1A, 1B, 1C, and 1D are explanatory views showing steps of a process for producing an embodiment of the carrier in accordance with the present invention, FIGS. 2A, 2B, and 2C are explanatory views showing steps of the process for producing the embodiment of the carrier in accordance with the present invention, FIG. 3 is a schematic sectional view showing a constitution of a bioreactor, FIG. 4 is an explanatory view showing an embodiment of the chip for surface plasmon resonance analysis in accordance with the present invention.

DETAILED DESCRIPTION OF THE INVENTION

Figure 5:
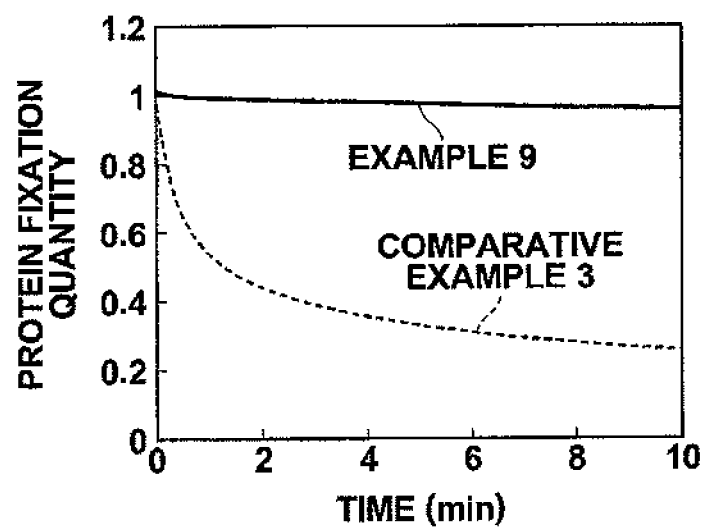
FIG. 5 is a graph showing alterations of a protein fixation quantity (a protein fixation rate) with the passage of time.

The carrier in accordance with the present invention comprises:
   i) the base plate,
   ii) the polymeric film, which has been bound on the surface of the base plate, and
   iii) the ligand, which has been bound with the polymeric film,
the ligand having been bound with the polymeric film at a density falling within the range of $1.0\times10^{16}$ pieces/mm$^3$ to $3.3\times10^{18}$ pieces/mm$^3$.

The constitution of the carrier in accordance with the present invention and how to form the constitution of the carrier (the activation) will be described hereinbelow. Steps of the process for producing an embodiment of the carrier in accordance with the present invention will then be described with reference to the accompanying drawings. Thereafter, how the carrier in accordance with the present invention is applied to the bioreactor and the chip for surface plasmon resonance analysis will be described.

(1) Base Plate

By way of example, in cases where the carrier in accordance with the present invention is to be applied to a surface plasmon resonance biosensor, ordinarily, the base plate of the carrier in accordance with the present invention may be constituted of a material, which is transparent with respect to a laser beam, e.g., optical glass, such as BK7, or a synthetic resin, such as a polymethyl methacrylate, a polyethylene terephthalate, a polycarbonate, or a cycloolefin polymer. The base plate should preferably be constituted of a material, which has not exhibit anisotropy with respect to polarization and has good processability.

The metal film is located on the base plate. The term "located on a base plate" as used herein embraces the cases wherein the metal film is located on the base plate so as to be in direct contact with the base plate, and the cases wherein, instead of being in direct contact with the base plate, the metal film is located on the base plate via a different layer. By way of example, in cases where the carrier in accordance with the present invention is to be applied to the surface plasmon resonance biosensor, the metal for constituting the metal film may be selected from a wide variety of metals, which enable the occurrence of the surface plasmon resonance. The metal for constituting the metal film should preferably be selected from free electron metals, such as gold, silver, copper, aluminum, and platinum, and should more preferably be gold. Each of the above-enumerated metals may be used alone, or at least two kinds of metals among the above-enumerated metals may be used in combination. Also, with adhesion characteristics with respect to the base plate being taken into consideration, an intervening layer constituted of chromium, or the like, may be located between the base plate and the layer constituted of the metal.

The film thickness of the metal film may be set at an arbitrary value. By way of example, in cases where the carrier in accordance with the present invention is to be applied to the surface plasmon resonance biosensor, the film thickness of the metal film should preferably fall within the range of 0.1 nm to 500 nm, and should more preferably fall within the range of 1 nm to 200 nm. If the film thickness of the metal film is larger than 500 nm, the surface plasmon phenomenon of the medium will not be capable of being detected sufficiently. In cases where the intervening layer constituted of chromium, or the like, is located between the base plate and the metal film, the thickness of the intervening layer should preferably fall within the range of 0.1 nm to 10 nm.

Also, in cases where the carrier in accordance with the present invention is to be applied to the bioreactor, the base plate may be constituted of glass, a metal oxide, or a synthetic resin, such as a sepharose, a polyethylene, a polystyrene, a poly(meth)acrylic acid, a poly(meth)acrylamide, a polymethyl(meth)acrylate, a polyethylene terephthalate, a polycarbonate, or a cycloolefin polymer. The base plate should preferably be constituted of a material, which has a high stability under the conditions of use of the bioreactor.

In cases where the carrier in accordance with the present invention is to be applied to the bioreactor, the carrier need not necessarily be provided with the metal film. In cases where the carrier is to be provided with the metal film, the metal for constituting the metal film may be selected from the metals enumerated above for the cases where the carrier in accordance with the present invention is to be applied to the biosensor. The film thickness of the metal film should preferably fall within the range of 0.1 nm to 1 μm, and should more preferably fall within the range of 1 nm to 100 nm. Also, as in cases where the carrier in accordance with the present invention is to be applied to the biosensor, the intervening layer constituted of chromium, or the like, may be located between the base plate and the layer constituted of the metal. The thickness of the intervening layer should preferably fall within the range of 0.1 nm to 10 nm.

(2) Polymeric Film

The polymeric film is bound with the metal film, which has been located on the base plate. The polymeric film may be constituted of a hydrophilic polymer, a hydrophobic polymer, or a combination of the hydrophilic polymer and the hydrophobic polymer with each other, and should preferably be constituted of the hydrophilic polymer. The polymeric film may be bound directly or indirectly with the metal film, which has been located on the base plate. The polymeric film should more preferably be constituted of a combination of a self-assembled monolayer forming molecule and the hydrophilic polymer with each other on the metal film, which has been located on the base plate. How the polymeric film is constituted of the combination of the self-assembled monolayer forming molecule and the hydrophilic polymer with each other will be described hereinbelow.

(2-1) Self-Assembled Monolayer Forming Molecule

The term "self-assembled monolayer" as used herein means the microfilm, such as a monolayer or an LB film, which has a configuration possessing predetermined order formed by a system, which the film material itself has, in a state in which fine control is not being applied from the exterior. With the self-assembly, a structure or a pattern, which is in good order over a long distance, is formed in a non-equilibrium state.

A technique for covering a metal film by use of self-assembled monolayers (SAMs) has been developed vigorously by Professor Whitesides of Harvard University, et al. The details of the technique for covering a metal film by use of self-assembled monolayers have been reported in, for example, Chemical Review, 105, 1103-1169 (2005). In cases where gold is employed as the metal, by use of an alkanethiol derivative, which may be represented by the general formula A-1 shown below, wherein n represents an integral number falling within the range of 3 to 20 and wherein X represents a functional group, as the organic layer forming compound, a monolayer having orientational characteristics is formed in a self-assembled manner in accordance with van der Weals force of the Au-S bond and the alkyl chain with each other. The self-assembled monolayer is prepared with a markedly simple technique, wherein the goldbase plate is dipped in a solution of the alkanethiol derivative. In cases where the self-assembled monolayer is formed by use of the compound, which may be represented by the general formula A-1, wherein X represents $NH_2$, it becomes possible for the gold surface to be covered with the organic layer having the amino group.

$HS(CH_2)_nX$          A-1

The alkanethiol having the amino group at the terminal may be a compound, in which the thiol group and the amino group is joined with each other via the alkyl chain, and which may be represented by the general formula A-2 shown below, wherein n represents an integral number falling within the range of 3 to 20. Alternatively, the alkanethiol having the amino group at the terminal may be a compound obtained from a reaction of an alkanethiol, which has a carboxyl group at the terminal and which may be represented by the general formula A-3 shown below, wherein n represents an integral number falling within the range of 3 to 20, with a large excess of a hydrazide or a diamine. As another alternative, the alkanethiol having the amino group at the terminal may be a compound obtained from a reaction of an alkanethiol, which has the carboxyl group at the terminal and which may be represented by the general formula A-4 shown below, wherein each of two n's independently represents an integral number falling within the range of 1 to 20, with a large excess of the hydrazide or the diamine. The reaction of the alkanethiol, which has the carboxyl group at the terminal, with a large excess of the hydrazide or the diamine may be performed in a solution state. Alternatively, after the alkanethiol, which has the carboxyl group at the terminal, has been bound on the base plate surface, the alkanethiol may be caused to undergo the reaction with a large excess of the hydrazide or the diamine.

$HS(CH_2)_nNH_2$          A-2

$HS(CH_2)_nCOOH$          A-3

$HS(CH_2)_n(OCH_2CH_2)_nOCH_2COOH$          A-4

In each of the general formulas A-2, A-3, and A-4, the repetition number of the alkyl group should preferably fall within the range of 3 to 20, should more preferably fall within the range of 3 to 16, and should most preferably fall within the range of 4 to 8. If the alkyl chain is markedly short, the self-assembled monolayer will not always be capable of being formed. If the alkyl chain is markedly long, the solubility in water will become low, and handling characteristics will become bad.

As a polyamine employed in the present invention, it is possible to employ an arbitrary compound. In the cases of the use on the biosensor surface or the bioreactor surface, a water-soluble polyamine is preferable. Examples of the water-soluble polyamines include aliphatic diamines, such as ethylenediamine, tetraethylenediamine, octamethylenediamine, decamethylenediamine, piperazine, triethylenediamine, diethylenetriamine, triethylenetetramine, dihexamethylenetriamine, and 1,4-diaminocyclohexane; and aromatic diamines, such as paraphenylenediamine, metaphenylenediamine, paraxylylenediamine, metaxylylenediamine, 4,4'-diaminobiphenyl, 4,4'-diaminodiphenylmethane, 4,4'-diaminodiphenyl, and 4,4'-diaminodiphenylsulfonic acid. From the view point of enhancement of hydrophilic characteristics of the biosensor surface or the bioreactor surface, it is also possible to use a compound, in which two amino groups have been joined with each other by an ethylene glycol unit. The diamine employed in the present invention should preferably be ethylenediamine or a compound, which may be represented by the general formula A-5 shown below, wherein each of n and m independently represents an integral number falling within the range of 1 to 20. The diamine employed in the present invention should more preferably be ethylenediamine or 1,2-bis(aminoethoxy)ethane, which may be represented by the general formula A-5 shown below, wherein n=2, and m=1.

$$H_2N(CH_2)_n(OCH_2CH_2)_mO(CH_2)_nNH_2 \qquad \text{A-5}$$

The alkanethiol having the amino group is alone capable of forming the self-assembled monolayer. Also, the alkanethiol having the amino group is capable of forming the self-assembled monolayer by being mixed with a different kind of an alkanethiol. In the cases of the use on the biosensor surface, the different kind of the alkanethiol described above should preferably be a compound, which is capable of suppressing non-specific adsorption of the physiologically active substance. The self-assembled monolayer, which is capable of suppressing the non-specific adsorption of the physiologically active substance, has been studied in detail by Professor Whitesides described above, et al. It has been reported that a self-assembled monolayer having been formed from an alkanethiol having a hydrophilic group is efficient for the suppression of the non-specific adsorption of the physiologically active substance. (Reference may be made to Langmuir, 17, 2841-2850, 5605-5620, 6336-6343 (2001).)

In the present invention, as the alkanethiol for forming the mixed monolayer together with the alkanethiol having the amino group, the compound described in the aforesaid thesis may be used appropriately. From the view point of good performance for the suppression of the non-specific adsorption and high availability, as the alkanethiol for forming the mixed monolayer together with the alkanethiol having the amino group, there should preferably be used an aikanethiol, which has a hydroxyl group and which may be represented by the general formula A-6 shown below, wherein n represents an integral number falling within the range of 3 to 20, or an alkanethiol, which has the ethylene glycol unit and which may be represented by the general formula A-7 shown below, wherein each of n and m independently represents an integral number falling within the range of 1 to 20. In the general formula A-6, n should preferably represent an integral number of at least 5, should more preferably represent an integral number of at least 10, should particularly preferably represent an integral number falling within the range of 10 to 30, and should most preferably represent an integral number falling within the range of 10 to 16.

$$HS(CH_2)_nOH \qquad \text{A-6}$$

$$HS(CH_2)_n(OCH_2CH_2)_mOH \qquad \text{A-7}$$

In cases where the alkanethiol having the amino group is to be used for forming the self-assembled monolayer by being mixed with the different kind of the alkanethiol, the repetition number of the alkyl group in each of the general formulas A-2, A-3, and A-4 should preferably fall within the range of 4 to 20, should more preferably fall within the range of 4 to 16, and should most preferably fall within the range of 4 to 10. Also, the repetition number of the alkyl group in each of the general formulas A-6 and A-7 should preferably fall within the range of 3 to 16, should more preferably fall within the range of 3 to 12, and should most preferably fall within the range of 3 to 8.

In the present invention, the alkanethiol having the amino group and the alkanethiol having the hydroxyl group are capable of being mixed in arbitrary proportions. However, if the proportion of the alkanethiol having the amino group is low, the binding quantity of the hydrophilic polymer, which will be described later, will become small. Also, if the proportion of the alkanethiol having the hydroxyl group is low, the performance for the suppression of the non-specific adsorption will become bad. Therefore, the mixing ratio of the alkanethiol having the amino group to the alkanethiol having the hydroxyl group should preferably fall within the range between 1/1 and 1/1,000,000, should more preferably fall within the range between 1 and 1/1,000, and should most preferably fall within the range between 1 and 1/10. From the view point of suppression of steric hindrance in the cases of the reaction with a polymer containing a carboxyl group having been subjected to activating esterification, a molecular length of the alkanethiol having the amino group should preferably be longer than the molecular length of the alkanethiol having the hydroxyl group.

As the alkanethiol employed in the present invention, it is possible to use a compound having been synthesized in accordance with general remarks made by Professor Grzybowski of Northwestern University (Curr. Org. Chem., 8, 1763-1797 (2004)) and a literature cited therein. Alternatively, a commercially available compound may be used. The compounds described above are capable of being supplied by Dojin Kagaku K.K., Aldrich, SensoPath Technologies, and Frontier Scientific Inc. In the present invention, a disulfide compound, which is an oxidation product of the alkanethiol, is capable of being employed as in the cases of the alkanethiol.

(2-2) Hydrophilic Polymer

Examples of the hydrophilic polymers, which may be employed in the present invention, include gelatin, agarose, chitosan, dextran, carrageenan, alginic acid, starch, cellulose, and derivatives of the above-enumerated hydrophilic polymers, such as carboxymethyl derivatives; and water-swelling organic polymers, such as a polyvinyl alcohol, a polyacrylic acid, a polyacrylamide, a polyethylene glycol, and derivatives of the above-enumerated water-swelling organic polymers.

As the hydrophilic polymer, which may be employed in the present invention, it is also possible to use a carboxyl group-containing synthetic polymer or a carboxyl group-containing polysaccharide. Examples of the carboxyl group-containing synthetic polymers include a polyacrylic acid, a polymethacrylic acid, and copolymers thereof, e.g. copolymers as described in Japanese Unexamined Patent Publication No. 59(1984)-053836, page 3, line 20 to page 6, line 49, and Japanese Unexamined Patent Publication No. 59(1984)-071048, page 3, line 41 to page 7, line 54, such as a methacrylic acid copolymer, an acrylic acid copolymer, an itaconic acid copolymer, a crotonic acid copolymer, a maleic acid copolymer, a partially esterified maleic acid copolymer, and an addition product of a polymer having a hydroxyl group and an acid anhydride. The carboxyl group-containing polysaccharide may be an extract from a natural plant, a product of microorganism fermentation, a synthetic product obtained with an enzyme, or a chemical synthetic product. Examples of the carboxyl group-containing polysaccharides include hyaluronic acid, chondroitin sulfate, heparin, dermatan sulfate, carboxymethyl cellulose, carboxyethyl cellulose, cellouronic acid, carboxymethyl chitin, carboxymethyl dextran, and carboxymethyl starch. As the carboxyl group-containing polysaccharide, it is possible to use a commercially available compound. Examples of the commercially available compounds include CMD (carboxymethyl dextran), CMD-L, and CMD-D40 (which are supplied by Meito Sangyo Co., Ltd.); sodium carboxymethyl cellulose (which is supplied by Wako Pure Chemical Industries, Ltd.); and sodium alginate (which is supplied by Wako Pure Chemical Industries, Ltd.).

No limitation is imposed upon a molecular weight of the hydrophilic polymer employed in the present invention. Ordinarily, the molecular weight of the hydrophilic polymer employed in the present invention should preferably fall within the range of 200 to 5,000,000, and should more preferably fall within the range of 10,000 to 2,000,000.

The hydrophilic polymer described above may be bound on the base plate via the self-assembled monolayer or a hydrophobic polymer as will be described later. Alternatively, the hydrophilic polymer described above may be formed directly on the base plate from a solution containing a monomer. Also, the hydrophilic polymer described above may be subjected to crosslinking. The crosslinking of the hydrophilic polymer may be performed in accordance with a known technique.

As for the hydrophilic polymer, which is to be bound on the biosensor surface or the bioreactor surface, the film thickness of the hydrophilic polymer in an aqueous solution should preferably fall within the range of 1 nm to 0.5 mm, and should more preferably fall within the range of 1 nm to 1 μm. If the film thickness is markedly small, the fixation quantity of the physiologically active substance will become small, and the interaction with the sample substance will not be always capable of occurring. If the film thickness is markedly large, obstruction will occur with respect to the diffusion of the sample substance within the film. The film thickness of the hydrophilic polymer in the aqueous solution is capable of being evaluated with AFM, ellipsometry, or the like.

(2-3) Activation of Hydrophilic Polymer

In cases where the polymer containing the carboxyl group is used as the hydrophilic polymer, with a technique for activating the carboxyl group, the polymer is capable of being bound on the base plate, which has been covered with the self-assembled monolayer. As the technique for activating the polymer containing the carboxyl group, it is possible to use appropriately a known technique, e.g., a technique for activating with 1-(3-dimethylaminopropyl)-3-ethylcarbodiimide (EDC), which is a water-soluble carbodiimide, and N-hydroxysuccinimide (NHS), or a technique for activating with EDC alone. In cases where the polymer containing the carboxyl group, which polymer has been activated with the technique described above, is caused to react with the base plate having the amino group, the hydrophilic polymer is capable of being bound on the base plate.

Also, as the technique for activating the polymer containing the carboxyl group, it is possible to use a technique wherein a nitrogen-containing compound is utilized. Specifically, it is possible to utilize a nitrogen-containing compound, which may be represented by the general formula (Ia) or the general formula (Ib) shown below, wherein each of $R^1$ and $R^2$ independently represents an electron-attracting group (e.g., a carbonyl group, an aromatic ring, or a nitrogen atom), or $R^1$ and $R^2$ jointly represent a five-membered ring or a six-membered ring, A represents a carbon atom or a phosphorus atom, M represents an (n−1)-valent element, and X represents a halogen atom.

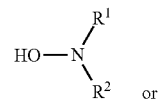

(Ia)

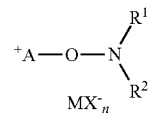

(Ib)

In this case, each of $R^1$ and $R^2$ may independently represent a carbonyl group, a carbon atom, or a nitrogen atom, which may have a substituent group. Preferably, $R^1$ and $R^2$ jointly represent the five-membered ring or the six-membered ring. Particularly preferably, there is furnished hydroxysuccinic acid, hydroxyphthalic acid, 1-hydroxybenzotriazole, 3,4-dihydroxy-3-hydroxy-4-oxo-1,2,3-benzotriazine, and derivatives of the above-enumerated compounds.

It is also possible to utilize preferably the nitrogen-containing compounds, which may be represented by the formulas shown below.

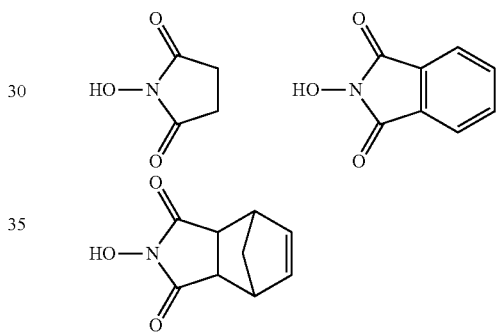

Further, as the nitrogen-containing compound, it is possible to utilize preferably the compound, which may be represented by the general formula (I) shown below, wherein each of Y and Z independently represents CH or a nitrogen atom.

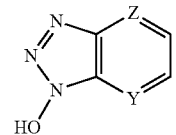

General formula (I)

Preferable examples of the compounds, which may be represented by the general formula (I), include the compounds, which may be represented by the formulas shown below.

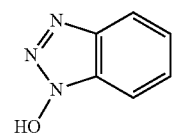 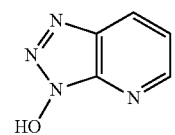

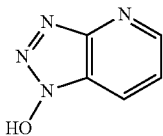

Furthermore, as the nitrogen-containing compound, it is possible to utilize preferably the compound, which may be represented by the formula shown below.

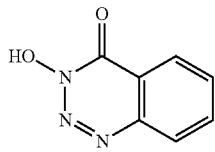 [SMILES: O=c1c2ccccc2nnn1O]

Also, as the nitrogen-containing compound, it is possible to utilize preferably the compound, which may be represented by the general formula (II) shown below, wherein A represents a carbon atom or a phosphorus atom, which has a substituent group, each of Y and Z independently represents CH or a nitrogen atom, M represents an (n−1)-valent element, and X represents a halogen atom.

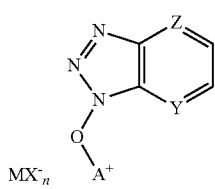

General formula (II)

In this case, the substituent group, which the carbon atom or the phosphorus atom has, should preferably be an amino group having a substituent group, and should more preferably be a dialkylamino group, such as a dimethylamino group, or a pyrrolidino group. The (n−1)-valent element, which is represented by M, may be, for example, a phosphorus atom, a boron atom, or an arsenic atom, and should preferably be the phosphorus atom. The halogen atom, which is represented by X, may be a fluorine atom, a chlorine atom, a bromine atom, or an iodine atom, and should preferably be the fluorine atom.

Preferable examples of the compounds, which may be represented by the general formula (II), include the compounds, which may be represented by the formulas shown below.

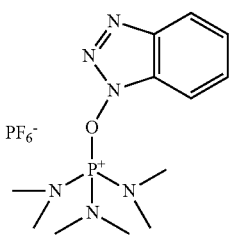
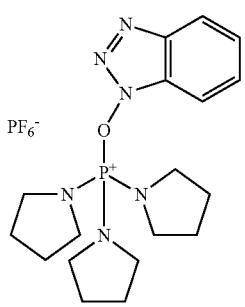

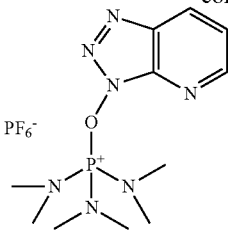
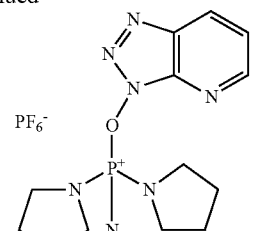

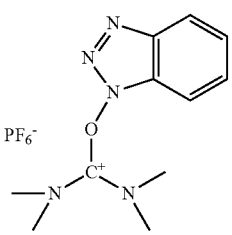
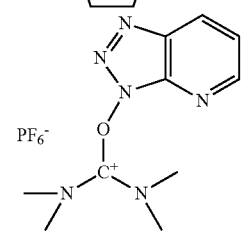

Further, as the nitrogen-containing compound, it is possible to utilize preferably the compound, which may be represented by the general formula (III) shown below, wherein A represents a carbon atom or a phosphorus atom, which has a substituent group, M represents an (n−1)-valent element, and X represents a halogen atom.

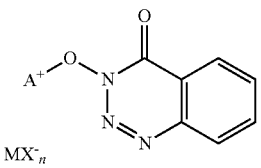

General formula (III)

A preferable example of the compound, which may be represented by the general formula (III), is the compound, which may be represented by the formula shown below.

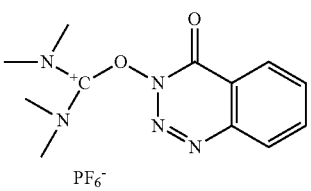

Further, as the technique for activating the polymer containing the carboxyl group, it is possible to use preferably a technique wherein a phenol derivative, which has an electron-attracting group, is utilized. In such cases, the electron-attracting group should preferably have the σ value of at least 0.3. Specifically, it is possible to utilize, for example, the compounds, which may be represented by the formulas shown below.

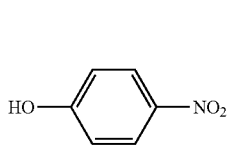
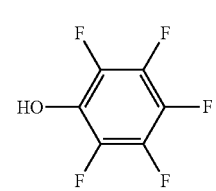

-continued

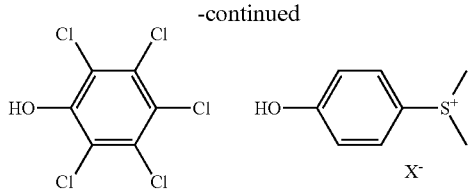

Furthermore, as the technique for activating the polymer containing the carboxyl group, it is possible to use a technique wherein a carbodiimide derivative is utilized in combination. The carbodiimide derivative, which may be utilized in combination, should preferably be a water-soluble carbodiimide derivative, and should more preferably be the compound (1-ethyl-3-(3-dimethylaminopropyl)carbodiimide, hydrochloride), which may be represented by the formula shown below.

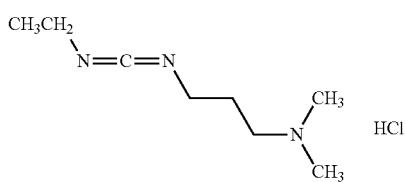

The carbodiimide derivative described above may be utilized in combination with the nitrogen-containing compound or the phenol derivative. Alternatively, when necessary, each of the carbodiimide derivative described above, the nitrogen-containing compound, and the phenol derivative may be utilized alone. There should preferably be utilized the combination of the carbodiimide derivative and the nitrogen-containing compound.

Also, as the technique for activating the polymer containing the carboxyl group, it is possible to use a technique wherein the compound, which may be represented by the formula shown below, is utilized. The compound, which may be represented by the formula shown below, may be utilized alone or in combination with the carbodiimide derivative, the nitrogen-containing compound, and/or the phenol derivative.

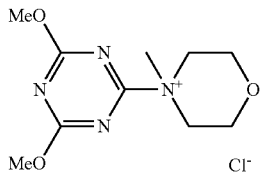

Further, as the technique for activating carboxylic acid in the polymer containing the carboxyl group, it is possible to use preferably a technique described in Japanese Unexamined Patent Publication No. 2006-058071, [0011] to [0022] (i.e., the technique, wherein a carboxyl group located on a surface of a base plate is activated by use of a compound selected from the group consisting of a uronium salt, a phosphonium salt, and a triazine derivative, which have specific structures, and wherein a carboxylic acid amido group is thereby formed). It is also possible to use preferably a technique described in Japanese Unexamined Patent Publication No. 2006-090781, [0011] to [0019] (i.e., the technique, wherein a carboxyl group located on a surface of a base plate is activated by use of a carbodiimide derivative or a salt thereof, wherein esterification is performed by use of a compound selected from the group consisting of a nitrogen-containing heteroaromatic compound having a hydroxyl group, a phenol derivative having an electron-attracting group, and an aromatic compound having a thiol group, wherein a reaction with an amine is performed, and wherein a carboxylic acid amido group is thereby formed).

The uronium salt, the phosphonium salt, and the triazine derivative, which have the specific structures, as described in Japanese Unexamined Patent Publication No. 2006-058071, are the uranium salt, which may be represented by the general formula 1 shown below, the phosphonium salt, which may be represented by the general formula 2 shown below, and the triazine derivative, which may be represented by the general formula 3 shown below, respectively.

General formula 1

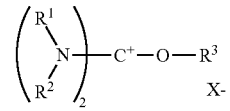

General formula 2

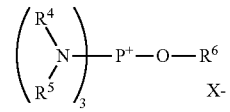

General formula 3

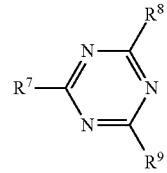

(In the general formula 1, each of $R^1$ and $R^2$ independently represents an alkyl group having one to six carbon atoms, or $R^1$ and $R^2$ jointly form an alkylene group having two to six carbon atoms and form a ring in conjunction with the N atom, $R^3$ represents an aromatic ring group having six to 20 carbon atoms or represents a heterocyclic ring group having at least one hetero atom, and $X^-$ represents an anion. In the general formula 2, each of $R^4$ and $R^5$ independently represents an alkyl group having one to six carbon atoms, or $R^4$ and $R^5$ jointly form an alkylene group having two to six carbon atoms and form a ring in conjunction with the N atom, $R^6$ represents an aromatic ring group having six to 20 carbon atoms or represents a heterocyclic ring group having at least one hetero atom, and $X^-$ represents an anion. In the general formula 3, $R^7$ represents an onium group, and each of $R^8$ and $R^9$ independently represents an electron-donating group.)

(2-4) Coating of Hydrophilic Polymer onto Base Plate

In the present invention, the polymer containing the carboxyl group having been subjected to activating esterification may be caused to undergo the reaction with the base plate in the form of a solution. Alternatively, the polymer containing the carboxyl group having been subjected to activating esterification may be applied to form a thin film on the base plate by use of a technique, such as a spin coating technique, and may be caused to undergo the reaction with the base plate in the state of the thin film. The polymer should preferably be caused to undergo the reaction with the base plate in the state of the thin film.

As described above, in the present invention, the polymer containing the carboxyl group having been subjected to activating esterification should preferably be caused to undergo the reaction with the base plate in the state of the thin film. As the technique for forming the thin film on the base plate, one of known techniques may be employed. Specifically, it is possible to employ an extrusion coating technique, a curtain coating technique, a casting technique, a screen printing technique, a spin coating technique, a spray coating technique, a slide beads coating technique, a slit and spin technique, a slit coating technique, a die coating technique, a dip coating technique, a knife coating technique, a blade coating technique, a flow coating technique, a roll coating technique, a wire bar boating technique, a transfer printing technique, or the like. The thin film forming techniques are described in, for example, "Coating Gijutsu No Shinpo" (Progress of Coating Technology), written by Yuji Harasaki, Sogo Gijutsu Center (1988); "Coating Gijutsu" (Coating Technology), Technical Information institute Co., Ltd. (1999); "Suisei Coating No Gijutsu" (Aqueous Coating Technology), CNC (2001); "Shinka Suru Yuki Hakumaku Seimaku-Hen" (Evolving Organic Thin Film, Film Formation Edition), Sumibe Techno Research Co., Ltd. (2004); and "Kobunshi Hyomen Kako Gaku" (Polymer Surface Processing Engineering), written by Akatsuki Iwamori, Gihodo Shuppan (2005). In the present invention, as the technique for forming the thin film on the base plate, the spray coating technique or the spin coating technique should preferably be employed, and the spin coating technique should more preferably be employed. With the spray coating technique or the spin coating technique, a coating film having a controlled film thickness is capable of being prepared easily.

(3) Ligand

The ligand is bound with the polymeric film. As the compound acting as the ligand, it is possible to employ various kinds of chelating agents. Preferable examples of the ligands include multidentate ligands, such as a nitrilotriacetic acid derivative (NTA) iminodiacetic acid, phenanthroline, terpyridine, bipyridine, triethylenetetramine, diethylenetriamine, tris(carboxymethyl)ethylenediamine, diethylenetriaminepentaacetic acid, polypyrazolylboric acid, 1,4,7-triazocyclononane, dimethylglyoxime, and diphenylglyoxime. The ligand should preferably be nitrilotriacetic acid, iminodiacetic acid, or derivatives thereof, and should more preferably be NTA, which is the quadridentate ligand. By way of example, in cases where the polymeric film is constituted of the hydrophilic polymer having the carboxyl group, the ligand is capable of being bound with the hydrophilic polymer with the processing wherein, after the carboxyl group has been activated, the compound acting as the ligand is caused to undergo the reaction with the hydrophilic polymer.

At the time of the binding of the ligand with the polymeric film, an organic solvent should preferably be used. In cases where the organic solvent is used, the ligand is capable of being bound with the polymeric film at a density falling within the range of $1.0 \times 10^{16}$ pieces/mm$^3$ to $3.3 \times 10^{18}$ pieces/mm$^3$. The density of the ligand should preferably fall within the range of $1.0 \times 10^{16}$ pieces/mm$^3$ to $3.3 \times 10^{18}$ pieces/mm$^3$, should more preferably fall within the range of $1.0 \times 10^{16}$ pieces/mm$^3$ to $1.8 \times 10^{17}$ pieces/mm$^3$, and should most preferably fall within the range of $3.5 \times 10^{16}$ pieces/mm$^3$ to $1.8 \times 10^{17}$ pieces/mm$^3$. However, as the film density becomes high, it will often occur that the physiologically active substance is not capable of easily entering into the film. Therefore, the density of the ligand should not be markedly high.

At the time of the binding of the ligand with the polymeric film, a base should preferably be used as an additive. In cases where the base is used, a binding rate of the ligand is capable of being enhanced even further. Preferable examples of the bases include DBU (1,8-diazabicyclo[5.4.0]undec-7-ene), DBN (1,5-diazabicyclo[4.3.0]non-5-ene), imidazole, methylimidazole, pyrimidine, pyridine, N,N-dimethyl-4-aminopyridine, picoline, 2,6-lutidine, quinoline, triethylamine, diisopropylethylamine, dimethylphenylamine, DABCO (1,4-diazabicyclo[2.2.2]octane, sodium hydroxide, potassium hydroxide, and cesium hydroxide. The base may be selected appropriately in accordance with the organic solvent used.

The proportion of the base used should preferably fall within the range of 0.1 mol % to 10,000 mol % with respect to the binding quantity of the ligand, should more preferably fall within the range of 100 mol % to 1,000 mol % with respect to the binding quantity of the ligand, and should most preferably fall within the range of 300 mol % to 500 mol % with respect to the binding quantity of the ligand.

The ligand density is capable of being found in the manner described below. Specifically, in cases where the ligand density is to be found with a measurement being made actually, after the ligand has been bound on the support, the metal ion is imparted, the number of pieces of the metal ion having been fixed on the support is calculated by use of an TOP analysis apparatus, or the like, and the number of pieces of the ligand per unit area is found in accordance with the number of pieces of the metal ion and the area of the region of the support, at which region the ligand has been bound. In cases where the ligand density is to be found with a calculation, the volume of the ligand may be found by use of a calculation software function, such as CHEM 3 D (supplied by CambridgeSoft), and the number of pieces of the ligand per unit area may thereby be calculated. In cases where the volume of the ligand is found by use of the calculation software function, since, e.g. as for NTA, the volume is estimated to be approximately 0.3 nm$^3$, it is theoretically not always possible to bind the ligand at a density higher than $3.3 \times 10^{18}$ pieces/mm$^3$. It is also possible to find the ligand density with the processing, wherein the physiologically active substance having been fixed is removed, and wherein thereafter the number of pieces of the metal ion is measured.

Preferable examples of the organic solvents include dimethyl sulfoxide, N,N-dimethylformamide, N,N-dimethylacetamide, acetonitrile, N-methylpyrrolidone, acetone, methyl ethyl ketone, methanol, ethanol, isopropyl alcohol, sec-butyl alcohol, tert-butyl alcohol, butyl cellosolve, tetrahydrofuran, and diglyme. From the view point of the ligand solubility and suppression of a side reaction, dimethyl sulfoxide or N,N-dimethylformamide should preferably be used as the organic solvent.

(4) Metal Ion

The metal ion may be selected from various kinds of metal ions capable of forming unsaturated metal complexes. From the view point of the stability of the metal complex obtained, the metal ion should preferably be a transition metal ion. Preferable examples of the metal ions include Ni(II), Cu(I), Cu(II), Co(II), Co(III), Fe(II), Fe(III), and Ga(III). The metal ion may be selected appropriately in accordance with the kind of the ligand. The metal ion should preferably be Ni(II), Cu(II), Co(III), or Fe(III), and should more preferably be Ni(II) or Cu(II). The metal ion varies in binding force in accordance with the valence number. In the cases of Co(II) or Fe(II), the binding force of the metal ion is capable of being altered through an alteration of the oxidation number of the metal ion by use of an oxidation-reduction technique as described in, for example, Japanese Unexamined Patent Publication No. 6 (1994)-157600 (corresponding to U.S. Pat. No. 5,439,829), [0037] and [0038].

As a combination of the metal ion and the ligand density, in cases where the metal ion is Cu(II), the ligand density should preferably be equal to at least $1.7 \times 10^{16}$ pieces/mm$^3$.

(5) Physiologically Active Substance

Examples of the physiologically active substances include an immune protein, an enzyme, a microorganism, nucleic acid, a low molecular weight organic compound, a non-immune protein, an immune globulin binding protein, a saccharide binding protein, a saccharide-recognizing saccharide chain, fatty acid or a fatty acid ester, and a polypeptide or an oligopeptide, which has ligand binding capability. The physiologically active substance is fixed on the base plate by the coordinate bond to the metal ion. The physiologically active substance may be selected from various kinds of substances, which have a functional group capable of coordinating with the metal ion, i.e. which has the metal coordinating capability. The metal coordinating capability is capable of being imparted easily through covalent bonding of the ligand having strong coordinating force.

The functional group may be a group, which has a nitrogen-containing heterocyclic ring, and which is capable of forming a metal complex in conjunction with the metal ion. The nitrogen-containing heterocyclic ring may have a monocyclic structure or a condensed ring structure, which contains a three- to seven-membered ring containing the nitrogen atom. The number of the nitrogen atom contained in the ring may be at least one. The nitrogen-containing heterocyclic ring should preferably contain a five-membered ring or a six-membered ring. Examples of the ligands having the nitrogen-containing heterocyclic rings include pyrrole, imidazole, pyrazole, oxazole, isoxazole, thiazole, isothiazole, 1,2,3-triazole, 1,2,4-triazole, 1,3,4-thiadiazole, tetrazole, pyridine, pyrazine, pyrimidine, pyridazine, 1,2,3-triazine, 1,2,4-triazine, 1,3,5-triazine, 1,2,4,5-tetrazine, azepine, azonine, quinoline, acridine, phenanthridine, indole, isoindole, carbazole, benzimidazole, 1,8-naphthyridine, purine, pteridine, benzotriazole, quinoxaline, quinazoline, perimidine, cinnoline, phthalazine, 1,10-phenanthroline, phenoxazine, phenothiazine, phenazine, 8-hydroxyquinoline, 8-mercaptoquinoline, 2,2'-bipyridine, 2,2'-dipyridylamine, di(2-picolylamine), 2,2',2''-terpyridine, porphyrine, phthalocyanine, and derivatives of the above-enumerated compounds. From the view point of the stability of the metal complex obtained, the ligand having the nitrogen-containing heterocyclic ring should preferably be pyrrole, imidazole, pyrazole, oxazole, thiazole, pyridine, or a derivative of one of the above-enumerated compounds.

For the advantages in that the introduction by use of an amino acid automatic synthesizing apparatus or the introduction by genetic engineering is easy, the functional group should preferably be the imidazole group. The length of the so-called "His-tag," in which histidine (His) having the imidazole group has been introduced as the functional site, should preferably be as large as possible, and the number of pieces of the imidazole group should more preferably fall within the range of 6 to 100. Histidine may be continuous as in the cases of a pattern of His-His-His-His. Alternatively, for example, a different structure may intervene as in the cases of a pattern of His-His-o-His-His.

The term "fixation of a physiologically active substance being performed at multiple points" as used herein means that the binding of the ligand and the metal ion with each other and the binding of the nitrogen-containing heterocyclic ring group, which is contained in His-tag, and the metal ion with each other are performed at multiple pieces of the metal ion. In cases where the density of the ligand per unit area is set to be high, and/or in cases where the length of His-tag is set to be long, the bindings described above are capable of being performed at multiple pieces of the metal ion.

(6) Fixation of Physiologically Active Substance

The fixation of the physiologically active substance may be performed with processing for coating a solution, which contains the physiologically active substance. The term "coating" as used herein embraces the dipping technique. In cases where the physiologically active substance has the nitrogen-containing heterocyclic ring group, the nitrogen-containing heterocyclic ring of the physiologically active substance coordinates with the metal ion to form a complex, and the physiologically active substance is thereby fixed (as illustrated in FIG. 2C).

In cases where the metal ion and the nitrogen-containing heterocyclic ring group of the physiologically active substance are imparted to the ligand, which has been bound with the support, (i) the ligand, (ii) the nitrogen-containing heterocyclic ring group of the physiologically active substance, and (iii) a water molecule or a hydroxide ion coordinate with the metal ion to form the complex.

For example, in cases where NTA is utilized as the ligand, and a metal ion, which is capable of having a coordination number of six, is imparted, among the six coordination sites, four coordination sites are occupied by (i) the three carboxyl groups and one nitrogen atom, which NTA has, and the two remaining coordination sites are occupied by (ii) the nitrogen-containing heterocyclic ring group of the physiologically active substance and (iii) a water molecule or a hydroxide ion, or the like. A hexacoordinate complex is thereby formed.

In cases where iminodiacetic acid is utilized as the ligand, and a metal ion, which is capable of having a coordination number of six, is imparted, among the six coordination sites, three coordination sites are occupied by (i) the two carboxyl groups and one nitrogen atom, which iminodiacetic acid has, and the three remaining coordination sites are occupied by (ii) the nitrogen-containing heterocyclic ring group of the physiologically active substance and (iii) a water molecule or a hydroxide ion, or the like. A hexacoordinate complex is thereby formed.

In the examples described above, the metal ion, which is capable of having a coordination number of six, is employed. However, the coordination number may be at least seven. Alternatively, the coordination number may be at most five. Also, the carboxyl groups for the formation of the complex need not necessarily be supplied by one piece of the ligand, and the carboxyl groups may be supplied by multiple pieces of the ligand and may thus form the complex.

(7) Production of Carrier

A process for producing an embodiment of the carrier in accordance with the present invention will be described hereinbelow with reference to the accompanying drawings. FIGS. 1A, 1B, 1C, and 1D are explanatory views showing steps of the process for producing the embodiment of the carrier in accordance with the present invention, which steps range from the formation of the metal film to the binding of the ligand with the polymeric film. FIGS. 2A, 2B, and 2C are explanatory views showing steps of the process for producing the embodiment of the carrier in accordance with the present invention, which steps range from the fixation of the metal ion to the ligand to the fixation of the physiologically active substance to the metal ion. In FIGS. 2A, 2B, and 2C, as an aid in facilitating the explanation of the binding of the ligand, the fixation of the metal ion, and the fixation of the physiologically active substance, the ligand is illustrated as an enlarged view. Also, by way of example, NTA is employed as the ligand, Ni(II) is employed as the metal ion, and a protein having His-tag is employed as the physiologically active substance (indicated by P in FIGS. 2B and 2C).

Firstly, as illustrated in FIG. 1A, the metal film is formed on the base plate. The formation of the metal film may be performed in accordance with a conventional technique, such as a sputtering technique, a vacuum evaporation technique, an ion plating technique, an electroplating technique, or an electroless plating technique. As described above, the intervening layer constituted of chromium, or the like, may be located between the base plate and the metal film. Thereafter, as illustrated in FIG. 1B, the SAM is formed on the metal film. As described above, the formation of the SAM is capable of being performed with the processing, wherein the base plate, on which the metal film has been formed, is dipped in a solution of an alkanethiol derivative, or the like.

Thereafter, as illustrated in FIG. 1C, the polymeric film is formed on the SAM. The surface of the base plate is covered with the amino group of the SAM. Therefore, in cases where the hydrophilic polymer containing the carboxyl group is utilized as the polymeric film, the carboxyl group may be activated, and the polymeric film may thus be fixed on the base plate, which has been covered with the SAM.

Thereafter, as illustrated in FIG. 1D, the ligand is bound with the polymeric film. As for the binding of the ligand, for example, in cases where the polymeric film is constituted of the hydrophilic polymer containing the carboxyl group, the carboxyl group may be activated, and the compound acting as the ligand may then be caused to undergo the reaction in an organic solvent. In this manner, the ligand is capable of being fixed to the hydrophilic polymer.

By way of example, in cases where the ligand illustrated in FIG. 1D is NTA, one piece of the carboxyl group of the polymeric film is substituted by three pieces of the carboxyl group as illustrated in FIG. 2A. As illustrated in FIG. 2B, Ni(II) is then added and caused to form the complex with the carboxyl group of NTA. In this state, the coordination sites of Ni(II) are not fulfilled perfectly by NTA. Thereafter, as illustrated in FIG. 2C, the protein having the imidazole group at the terminal is added to the resulting NTA-Ni(II) complex, the imidazole group coordinates with Ni(II). In FIG. 2C, as an aid in facilitating the explanation of the coordinating state, only four pieces of the imidazole group are illustrated. As described above, the number of pieces of the imidazole group should preferably fall within the range of 6 to 100.

After the protein having the imidazole group at the terminal has been fixed to Ni(II), washing processing with a buffer, an imidazole solution, or the like, should preferably be performed. With the washing processing, the protein, which has not been fixed to Ni(II) on the carrier, and impurities are capable of being removed, and the purification of the physiologically active substance having the imidazole group at the terminal is thus capable of being performed. Also, in cases where Cu(II) is employed as the metal ion, high retaining force is capable of being obtained between the physiologically active substance having the imidazole group at the terminal and Cu(II). Therefore, in such cases, with the washing processing, wherein a large quantity of the imidazole solution is caused to flow, the physiologically active substance having the imidazole group at the terminal does not flow off, and the purification with a higher accuracy than in the cases of Ni(II) is capable of being performed.

(8) Application of the Carrier in Accordance with the Present Invention

The carrier in accordance with the present invention is capable of being applied to a biosensor or a bioreactor. (Reference may be made to, for example, "Bioreactor Technology," 1988, CMC K.K.; and "Biochip And Biosensor," 2006, Kyoritsu Shuppan K.K.) The term "bioreactor" as used herein means the reactor, in which a biochemical reaction caused to occur by a bio-catalyst, such as an enzyme, a bacterium, a cell, or an organelle, is utilized for the production of a useful substance, the generation of energy, the decomposition of an environmental pollution substance, and the like. The term "biosensor" as used herein is interpreted in the broadest sense and means the sensor, in which an interaction between biomolecules is converted into a signal, such as an electric signal, and an objective substance is thereby analyzed and detected. The application of the carrier in accordance with the present invention to the biosensor and the application of the carrier in accordance with the present invention to the bioreactor will be described hereinbelow.

(8-1) Application to Bioreactor

In the cases of a bioreactor capable of performing the formation of a useful substance, the reaction, or the like, by use of an insoluble carrier, to which an enzyme has been fixed (as described in, for example, Japanese Utility Model Publication No. 4(1992)-18398 or 4(1992)-18399), as the insoluble carrier, it is possible to apply the carrier in accordance with the present invention, for example, the carrier comprising: (i) the base plate (e.g., a porous material, such as a ceramic material or a polysulfone material), (ii) the polymeric film, which has been bound on the surface of the base plate, (iii) the ligand, which has been bound with the polymeric film, (iv) the metal ion, which has been fixed to the ligand, and (v) the enzyme, which has been fixed to the metal ion.

A constitution of an ordinary bioreactor will be described hereinbelow with reference to FIG. 3. FIG. 3 is a schematic sectional view showing a constitution of a bioreactor. As illustrated in FIG. 3, the bioreactor comprises a solution inlet 1 and a solution outlet 2, which are located at the opposite ends of a housing 3. A plurality of tubular enzyme fixed films 4, 4, . . . are located within the bioreactor. The space between the housing 3 and the tubular enzyme fixed films 4, 4, . . . and the space between the tubular enzyme fixed films 4, 4, . . . are secured by a sealer 5, and the tubular enzyme fixed films 4, 4, . . . are secured within the housing 3. A tubular enzyme fixed film 4a is located such that the inside region is in communication with the solution inlet 1 at one end, and such that the other end is sealed by the sealer 5 and is blocked from the solution outlet 2. Also, a tubular enzyme fixed film 4b is located such that the inside region is in communication with the solution outlet 2 at one end, and such that the other end is sealed by the sealer 5 and is blocked from the solution inlet 1.

At the time at which a solution is injected under pressure through the solution inlet 1 into the bioreactor, the solution is fed into the inside region of the tubular enzyme fixed film 4a. While the solution is penetrating through the tubular enzyme fixed film 4a, the solution is brought into a first stage of contact with the enzyme having been fixed to the tubular enzyme fixed film 4a. The solution having penetrated through the tubular enzyme fixed film 4a is then fed into the inside region of the tubular enzyme fixed film 4b. While the solution is penetrating through the tubular enzyme fixed film 4b, the solution is brought into a second stage of contact with the enzyme having been fixed to the tubular enzyme fixed film 4b. By the contact described above, the reaction of the fixed enzyme and the solution with each other is capable of being performed. With the carrier in accordance with the present invention, in the cases of the bioreactor in which the reaction is performed under pressure, the enzyme is capable of being fixed reliably.

In the example described above, the fixation of the enzyme to the tubular enzyme fixed films 4, 4, . . . has been performed previously before the tubular enzyme fixed films 4, 4, . . . are accommodated within the housing 3. Alternatively, the fixation of the enzyme to the tubular enzyme fixed films 4, 4, . . . may be performed after the tubular enzyme fixed films 4, 4, . . . has been accommodated within the housing 3.

(8-2) Application to Biosensor

An ordinary biosensor is constituted of a receptor site, which recognizes a chemical substance to be detected, and a transducer site, which transduces a physical change or a chemical change, which arises at the receptor site, into an electric signal. An organism contains various combinations of substances, which have affinity with each other, such as a combination of an enzyme and a substrate, a combination of an enzyme and a coenzyme, a combination of an antigen and an antibody, and a combination of a hormone and a receptor. The biosensor utilizes the principle such that one of the substances, which have the affinity with each other, is fixed to a base plate and utilized as a molecule recognizing substance, and such that the other substance is measured selectively.

For example, a surface plasmon resonance biosensor is constituted of a member containing a section, which transmits and reflects light having been irradiated from the sensor, and a member containing a section, which fixes a physiologically active substance. The carrier in accordance with the present invention is capable of being employed as the member containing the section, which fixes the physiologically active substance.

The surface plasmon resonance occurs due to the phenomenon such that an intensity of monochromatic light, which has been reflected from an interface between an optically transparent substance, such as glass, and a thin metal film layer, depends upon a refractive index of a sample located on the light radiating-out side of the thin metal film layer. Therefore, the sample is capable of being analyzed in accordance with the results of measurement of the intensity of the monochromatic light, which has been reflected from the interface described above.

As a surface plasmon analysis apparatus for analyzing characteristics of a substance, which is to be analyzed, by the utilization of the phenomenon, in which the surface plasmon is excited by a light wave, there may be mentioned an apparatus utilizing a system referred to as the Kretschmann arrangement. (The surface plasmon analysis apparatus utilizing the system referred to as the Kretschmann arrangement is described in, for example, Japanese Unexamined Patent Publication No. 6(1994)-167443.) Basically, the surface plasmon analysis apparatus utilizing the system referred to as the Kretschmann arrangement comprises: (i) a dielectric material block having, for example, a prism-like shape, (ii) a metal film, which is formed on one surface of the dielectric material block, and which is to be brought into contact with a substance to be analyzed, such as a liquid sample, (iii) a light source for producing a light beam, (iv) an optical system for irradiating the light beam to the dielectric material block at various different incidence angles such that a total reflection condition may be obtained at an interface between the dielectric material block and the metal film, and (v) photo detecting means for detecting the intensity of the light beam, which has been totally reflected from the interface described above, and thereby detecting the state of surface plasmon resonance, i.e. the state of attenuated total reflection.

In order for the various different incidence angles described above to be obtained, a light beam having a comparatively small beam diameter may be caused to impinge upon the aforesaid interface with the incidence angle being altered. Alternatively, a light beam having a comparatively large beam diameter may be caused to impinge upon the aforesaid interface in a state of converged light or in a state of divergent light, such that the light beam may contain components, which impinge at various different incidence angles upon the interface. In the former case, the reflected light beam, which is reflected from the interface with its reflection angle altering in accordance with the alteration of the incidence angle of the incident light beam, may be detected with a small photodetector, which moves by being interlocked with the alteration of the reflection angle, or may be detected with an area sensor extending in the direction of alteration of the reflection angle. In the latter case, the light beam may be detected with an area sensor extending in a direction such that the area sensor is capable of receiving all of the light beam components having been reflected from the interface at various different reflection angles.

With the surface plasmon analysis apparatus having the constitution described above, in cases where the light beam impinges at a specific incidence angle, which is not smaller than the total reflection angle, upon the metal film, an evanescent wave having an electric field distribution occurs in the substance to be analyzed, which is in contact with the metal film, and the surface plasmon is excited by the evanescent wave and at the interface between the metal film and the substance to be analyzed. In cases where the wave vector of the evanescent wave coincides with the wave vector of the surface plasmon, and wave number matching is thus obtained, the evanescent wave and the surface plasmon resonate, and energy of the light transfers to the surface plasmon. As a result, the intensity of the reflected light beam, which is totally reflected from the interface between the dielectric material block and the metal film, becomes markedly low. Ordinarily, the lowering of the intensity of the reflected light beam is detected as a dark line by the photo detecting means described above. The resonance described above occurs only in cases where the incident light beam is P-polarized light. Therefore, it is necessary for the incident light beam to be set previously so as to impinge upon the aforesaid metal film as the P-polarized light.

In cases where the wave number of the surface plasmon is found from the incidence angle at which the attenuated total reflection (ATR) occurs, i.e. from an attenuated total reflection angle (ATR angle) $\theta_{SP}$, a dielectric constant of the substance to be analyzed is capable of being calculated. Such that the ATR angle $\theta_{SP}$ may be measured accurately and with a wide dynamic range, a technique has been proposed, in which array-like photo detecting means is utilized in the aforesaid type of the surface plasmon analysis apparatus. (The proposed technique for utilizing the array-like photo detecting means is described in, for example, Japanese Unexamined Patent Publication No. 11(1999)-326194.) The array-like photo detecting means comprises a plurality of light receiving devices arrayed in a predetermined direction. The array-like photo detecting means is located in an orientation such that each of the light receiving devices is capable of receiving one of components of the light beam, which components have been totally reflected at various different reflection angles from the interface described above.

In such cases, the surface plasmon analysis apparatus is often provided with differentiation means for performing differentiation of signal components of a photo detection signal, each of which signal components is outputted from one of the light receiving devices of the aforesaid array-like photo detecting means, with respect to the array direction of the light receiving devices. Also, the ATR angle $\theta_{SP}$ is specified in accordance with differentiation values, which are outputted by the differentiation means, and the characteristics with regard to the refractive index of the substance to be analyzed are thereby calculated.

As a similar analysis apparatus utilizing the attenuated total reflection (ATR), a leaky mode analysis apparatus has heretofore been known. The leaky mode analysis apparatus is described in, for example, "Bunko Kenkyu" (Spectrum Research), Vol. 47, No. 1, pp. 21-23 and 26-27, 1998.) Basically, the leaky mode analysis apparatus comprises: (i) a dielectric material block having, for example, a prism-like shape, (ii) a cladding layer, which is formed on one surface of the dielectric material block, (iii) an optical waveguide layer, which is formed on the cladding layer, and which is to be brought into contact with a liquid sample, (iv) a light source for producing a light beam, (v) an optical system for irradiating the light beam to the dielectric material block at various different incidence angles such that a total reflection condition may be obtained at an interface between the dielectric material block and the cladding layer, and (vi) a photo detecting means for detecting the intensity of the light beam, which has been totally reflected from the interface described above, and thereby detecting the state of excitation of a guided mode, i.e. the state of attenuated total reflection.

With the leaky mode analysis apparatus having the constitution described above, in cases where the light beam impinges at an incidence angle, which is not smaller than the total reflection angle, upon the cladding layer via the dielectric material block, only the light having a certain specific wave number, which light has impinged at a specific incidence angle upon the cladding layer, is propagated in the guided mode in the optical waveguide layer after passing through the cladding layer. In cases where the guided mode is thus excited, approximately all of the incident light is taken into the optical waveguide layer. Therefore, in such cases, the attenuated total reflection occurs, and the intensity of the light totally reflected from the aforesaid interface becomes markedly low. Also, the wave number of the guided optical wave depends upon the refractive index of the substance to be analyzed, which is located on the optical waveguide layer. Therefore, in cases where the aforesaid specific incidence angle, which is associated with the occurrence of the attenuated total reflection, is detected, the refractive index of the substance to be analyzed and characteristics of the substance to be analyzed with regard to the refractive index of the substance to be analyzed are capable of being analyzed.

In the leaky mode analysis apparatus, the array-like photo detecting means described above may be utilized in order to detect the position of the dark line occurring in the reflected light due to the attenuated total reflection. Also, the differentiation means described above is often utilized together with the array-like photo detecting means.

In the fields of pharmaceutical research, and the like, the surface plasmon analysis apparatus and the leaky mode analysis apparatus described above are often utilized for random screening for finding out a specific substance, which is capable of undergoing the binding with a desired sensing substance. In such cases, the sensing substance acting as the substance to be analyzed is fixed to the aforesaid thin film layer (the metal film in the cases of the surface plasmon analysis apparatus, or the combination of the cladding layer and the optical waveguide layer with each other in the cases of the leaky mode analysis apparatus), and a liquid sample containing a test body in a solvent is introduced on the sensing substance. Also, at each of stages after the passage of predetermined periods of time, the aforesaid ATR angle $\theta_{SP}$ is measured.

In cases where the test body contained in the liquid sample is a substance capable of undergoing the binding with the sensing substance, the refractive index of the sensing substance alters with the passage of time. Therefore, the aforesaid ATR angle $\theta_{SP}$ is measured at each of the stages after the passage of the predetermined periods of time, and a judgment is made as to whether an alteration of the ATR angle $\theta_{SP}$ has or has not occurred. In this manner, the state of the binding of the test body with the sensing substance is capable of being detected, and a judgment is capable of being made in accordance with the result of the detection and as to whether the test body is or is not the specific substance capable of undergoing the binding with the sensing substance. Examples of the combinations of the specific substances and the sensing substances with each other include the combination of an antigen and an antibody with each other, and the combination of an antibody and a different antibody with each other. Specifically, for example, a rabbit anti-human IgG antibody may be fixed as the sensing substance to the surface of the thin film layer, and a human IgG antibody may be employed as the specific substance.

In order for the state of the binding of the test body with the sensing substance to be detected, the ATR angle $\theta_{SP}$ itself need not necessarily be detected. Alternatively, for example, the liquid sample may be introduced on the sensing substance, and thereafter the quantity of the alteration of the ATR angle $\theta_{SP}$ may be measured. Also, the state of the binding of the test body with the sensing substance may be detected in accordance with the quantity of the alteration of the ATR angle $\theta_{SP}$. In cases where the array-like photo detecting means and the differentiation means described above are utilized in the analysis apparatus utilizing the attenuated total reflection, since the quantity of the alteration of the differentiation value reflects the quantity of the alteration of the ATR angle $\theta_{SP}$, the state of the binding of the test body with the sensing substance is capable of being detected in accordance with the quantity of the alteration of the differentiation value. (Reference may be made to, for example, Japanese Unexamined Patent Publication No. 2003-172694 of the applicant.) In the analysis method and apparatus utilizing the attenuated total reflection as described above, a cup-shaped or laboratory dish-shaped analysis chip, in which the sensing substance has been fixed to the thin film layer having been formed previously on a bottom surface, is prepared. Also, the liquid sample containing the test body in the solvent is introduced into the analysis chip, and the quantity of the alteration of the ATR angle $\theta_{SP}$ is measured.

Also, an analysis apparatus utilizing the attenuated total reflection, wherein analyses with a plurality of analysis chips loaded on a turn table, or the like, are made successively, and wherein the analyses with respect to a plurality of samples are thus capable of being performed quickly, is described in, for example, Japanese Unexamined Patent Publication No. 2001-330560.

In cases where the chip for surface plasmon resonance analysis in accordance with the present invention is employed for the surface plasmon resonance analysis, the chip for surface plasmon resonance analysis in accordance with the present invention is capable of being employed as a part of each of various kinds of the surface plasmon resonance analysis apparatuses described above.

Further, the chip for surface plasmon resonance analysis in accordance with the present invention is capable of being employed as a chip in a biosensor, which is provided with, for example, a waveguide structure supported on a surface of a base plate, and which detects an alteration of the refractive index by use of the waveguide In such cases, the waveguide structure supported on the surface of the base plate is provided with a diffraction grating and, when necessary, an additional layer. The waveguide structure is constituted of a planar waveguide body, which is formed from a thin dielectric layer. A light beam having been converged to the waveguide body is guided by the total reflection into the thin dielectric layer. The propagation speed of the thus guided optical wave (hereinbelow referred to as the mode) takes a value of C/N, where C represents the light velocity in a vacuum, and N represents the effective refractive index of the mode guided in the waveguide body. The effective refractive index N at one surface is determined by the constitution of the waveguide body, and the effective refractive index N at the other surface is determined by the refractive index of a medium, which is adjacent to the thin waveguide layer. Conduction of the optical wave is performed not only in the thin planar layer, but also by a different waveguide structure, particularly a strip-like waveguide body. In such cases, the waveguide structure takes on the form of a strip-like film. For the biosensor, it is an important factor that the alteration of the effective refractive index N arises due to an alteration of the medium, which is adjacent to the waveguide layer, and alterations of the refractive index and the thickness of the waveguide layer itself or the additional layer, which is adjacent to the waveguide layer.

The constitution of the biosensor of the type described above is described in, for example, Japanese Patent Publication No. 6 (1994)-27703, page 4, line 48 to page 14, line 15, and FIGS. 1 to 8; and U.S. Pat. No. 6,829,073, column 6, line 31 to column 7, line 47, and FIG. 9A, 9B.

For example, in one aspect, a structure may be formed, wherein a waveguide layer, in which a thin layer is planar, is located on a base material (e.g., Pyrex glass (trade name)). The waveguide layer and the base material together form the so-called waveguide body. The waveguide layer may be constituted of a laminate of a plurality of layers, such as oxide layers (e.g., $SiO_2$, $SnO_2$, $Ta_2O_5$, $TiO_2$, $TiO_2$—$SiO_2$, $HfO_2$, $ZrO_2$, $Al_2O_3$, $Si_3N_4$, HfON, SiON, scandium oxide, and mixtures of the above-enumerated oxides) and plastic layers (e.g., a polystyrene, a polyethylene, and a polycarbonate). In order for a light beam to propagate in the waveguide layer through the total reflection, it is necessary that the refractive index of the waveguide layer is larger than the refractive index of the adjacent medium (such as the base material or the additional layer, which will be described later). A diffraction grating is located in the waveguide layer surface or the waveguide volume, which stands facing the base material or the substance to be analyzed. The diffraction grating is capable of being formed in the base plate by use of an embossing technique, a holography technique, or one of other techniques. Thereafter, a thin waveguide film having a higher refractive index is formed to cover the top surface of the diffraction grating. The diffraction grating has the function for converging the light beam impinging upon the waveguide layer, the function for radiating out the mode which is already being guided in the waveguide layer, and the function for transmitting a part of the mode to the travel direction and reflecting a part of the mode. The waveguide layer is set such that the grating region is covered by the additional layer. When necessary, the additional layer may be constituted of a multi-layer film. The additional layer may be imparted with the function for enabling selective detection of a substance contained in the substance to be analyzed. As a preferable example, a layer having the detecting function may be formed on the outermost surface of the additional layer. As the layer having the detecting function described above, it is possible to utilize the layer capable of fixing the physiologically active substance.

In a different aspect, an array of diffraction grating waveguides may be incorporated in a well of a micro-plate. (Reference may be made to, for example, PCT Japanese Publication No. 2007-501432.) Specifically, in cases where the diffraction grating waveguides are located in an array pattern at the well bottom surface of the micro-plate, it is possible to perform screening of drugs or chemical substances with a high throughput.

In cases where the diffraction grating waveguides are utilized, such that the detection of the physiologically active substance on the top layer (the detecting region) of the diffraction grating waveguides may be capable of being performed, an incident light beam and a reflected light beam are detected, and an alteration of the refraction characteristics is detected. For such purposes, at least one light source (e.g., a laser or a diode) and at least one detector (e.g., a spectrometer, a CCD camera, or one of other photodetectors) are capable of being utilized. As the technique for measuring the alteration of the refractive index, one of two different operation modes, i.e. a spectrometric technique and an angle technique, may be utilized. With the spectrometric technique, a broad-band beam is sent as the incident light beam to the diffraction grating waveguide, and the reflected light beam is collected and measured with, for example, a spectrometer. With the observation of a spectrum position of a resonance wavelength (peak), it is possible to measure the alteration of the refractive index, i.e. the binding, at the surface of the diffraction grading waveguide or at the position in the vicinity of the surface of the diffraction grading waveguide. With the angle technique, a light beam nominally having a single wavelength is converged so as to form a certain range of irradiation angle and is irradiated to the diffraction grating waveguide. The resulting reflected light is measured with a CCD camera or one of other photodetectors. With the measurement of the position of a resonance angle reflected by the diffraction grating waveguide, it is possible to measure the alteration of the refractive index, i.e. the binding, at the surface of the diffraction grating waveguide or at the position in the vicinity of the surface of the diffraction grating waveguide.

The chip for surface plasmon resonance analysis in accordance with the present invention will be described herein below. The chip for surface plasmon resonance analysis in accordance with the present invention comprises:

i) the sensor chip base plate, ii) the metal film, which has been located on the surface of the sensor chip base plate, iii) the water-soluble polymeric film, which has been bound with the metal film, iv) the ligand, which has been bound with the water-soluble polymeric film, v) the metal ion, which has coordinated with the ligand, and vi) the physiologically active substance, which has been fixed to the metal ion, the ligand having been bound with the water-soluble polymeric film at a density falling within the range of $1.0 \times 10^{16}$ pieces/mm$^3$ to $3.3 \times 10^{18}$ pieces/mm$^3$, the physiologically active substance having at least seven histidine units, each of which is capable of coordinating with the metal ion, the physiologically active substance having been fixed to the metal ion via each of the histidine units.

An embodiment of the chip for surface plasmon resonance analysis in accordance with the present invention will be described hereinbelow with reference to FIG. 4. FIG. 4 is an explanatory view showing an embodiment of the chip for surface plasmon resonance analysis in accordance with the present invention. In FIG. 4, as an aid in facilitating the explanation of the binding state, a part of the ligand is illustrated as an enlarged view. Also, by way of example, NTA is employed as the ligand, Ni(II) is employed as the metal ion, and a protein having the histidine units is employed as the physiologically active substance (indicated by P in FIG. 4). Further, FIG. 4 illustrates the state, in which each of two pieces of NTA has been bound with one set of histidine units.

The chip for surface plasmon resonance analysis illustrated in FIG. 4 comprises the sensor chip base plate provided with the metal film, which has been located on the surface of the sensor chip base plate. The chip for surface plasmon resonance analysis also comprises the water-soluble polymeric film, which has been bound with the metal film. The chip for surface plasmon resonance analysis further comprises the ligand (NTA), which has been supported by the water-soluble polymeric film. The chip for surface plasmon resonance analysis still further comprises the metal ion (Ni(II)), which has coordinated with the ligand. The chip for surface plasmon resonance analysis also comprises the physiologically active substance, which has been fixed to the metal ion. The ligand has been bound with the water-soluble polymeric film at a density falling within the range of $1.0 \times 10^{16}$ pieces/mm$^3$ to $3.3 \times 10^{18}$ pieces/mm$^3$. The physiologically active substance has at least seven histidine units, each of which is capable of coordinating with the metal ion. Further, the physiologically active substance has been fixed to the metal ion via each of the histidine units. By way of example, in this embodiment, the water-soluble polymeric film is constituted of a combination of the self-assembled monolayer (SAM) and a water-soluble polymer with each other. As described above, the physiologically active substance has at least seven histidine units. In FIG. 4, as an aid in clearly illustrating the binding state, only four histidine units are shown.

The base plate and the metal film employed for the chip for surface plasmon resonance analysis in accordance with the present invention may be of the same types as those described above under "(1) Base plate" for the carrier in accordance with the present invention. The water-soluble polymeric film is bound with the metal film, which has been located on the base plate. The polymeric film should more preferably be constituted of the combination of the self-assembled monolayer forming molecule and the water-soluble polymer with each other on the metal film, which has been located on the base plate. The self-assembled monolayer forming molecule may be of the same type as that described above under "(2-1) Self-assembled monolayer forming molecule" for the carrier in accordance with the present invention.

The water-soluble polymer employed for the chip for surface plasmon resonance analysis in accordance with the present invention may be of the same type as that described above under "(2-2) Hydrophilic polymer" for the carrier in accordance with the present invention. As for the water-soluble polymer, which is to be bound on the biosensor surface, the film thickness of the water-soluble polymer in an aqueous solution should preferably fall within the range of 1 nm to 300 nm. If the film thickness is markedly small, the fixation quantity of the physiologically active substance will become small. Also, if the film thickness is markedly small, the hydration layer on the biosensor surface will become thin, and therefore the interaction with the sample substance will not be always capable of detected easily due to denaturation of the physiologically active substance itself. If the film thickness is markedly large, obstruction will occur with respect to the diffusion of the sample substance within the film. Also, particularly, in cases where the detection of the interaction is to be performed from the side opposite to the water-soluble polymer binding surface of the biosensor base plate, the distance from the detection surface to the interaction forming region will become long, and therefore the detection sensitivity will not be capable of being kept high. The film thickness of the water-soluble polymer in the aqueous solution is capable of being evaluated with the AFM, the ellipsometry, or the like.

The binding quantity of the water-soluble polymer, which is bound on the biosensor surface, should preferably fall within the range of 3 ng/mm$^2$ to 30 ng/mm$^2$, should more preferably fall within the range of 3 ng/mm$^2$ to 20 ng/mm$^2$, and should most preferably fall within the range of 3 ng/mm$^2$ to 15 ng/mm$^2$. Alternatively, the film thickness of the water-soluble polymer should preferably fall within the range of 3 nm to 30 nm, should more preferably fall within the range of 3 nm to 20 nm, and should most preferably fall within the range of 3 nm to 15 nm. As for the binding quantity of the water-soluble polymer, it is possible to utilize the value having been detected with one of various film thickness measuring techniques, various weight measuring techniques, and the like. Examples of the film thickness measuring techniques include the techniques with the interatomic force microscope (AFM); a scanning type probe microscope (SPM), such as a scanning type tunnel microscope (STM); an electron microscope, such as a transmission type electron microscope (TEM), a scanning type electron microscope (SEM), or a scanning type transmission electron microscope (STEM); and the ellipsometry technique.

The activation of the water-soluble polymer employed for the chip for surface plasmon resonance analysis in accordance with the present invention may be performed in the same manner as that described above under "(2-3) Activation of hydrophilic polymer" for the carrier in accordance with the present invention. Also, the coating of the water-soluble polymer, which may be employed for the chip for surface plasmon resonance analysis in accordance with the present invention, onto the base plate may be performed in the same manner as that described above under "(2-4) Coating of hydrophilic polymer onto base plate" for the carrier in accordance with the present invention. Further, the ligand and the metal ion, which may be employed for the chip for surface plasmon resonance analysis in accordance with the present invention, may be of the same types as those described above under "(3) Ligand" and "(4) Metal ion" for the carrier in accordance with the present invention.

The physiologically active substance, which may be employed for the chip for surface plasmon resonance analysis in accordance with the present invention, may be of the same type as that described above under "(5) Physiologically active substance" for the carrier in accordance with the present invention. Examples of the physiologically active substances include an immune protein, an enzyme, a microorganism, nucleic acid, a low molecular weight organic compound, a non-immune protein, an immune globulin binding protein, a saccharide binding protein, a saccharide-recognizing saccharide chain, fatty acid or a fatty acid ester, and a polypeptide or an oligopeptide, which has ligand binding capability. The physiologically active substance is fixed on the base plate by the coordinate bond to the metal ion. The physiologically active substance has at least seven histidine units, each of which is capable of coordinating with the metal ion. From the view point of obtaining strong fixation, the physiologically active substance should preferably have at least eight histidine units. Also, the number of the histidine units should more preferably be at most 100. If the number of the histidine units is larger than 100, the size of the histidine units themselves will give rise to obstruction of the activity of the physiologically active substance. The term "His-tag" as used herein means the histidine unit.

As described above under "(6) Fixation of physiologically active substance" for the carrier in accordance with the present invention, the fixation of the physiologically active substance, which may be employed for the chip for surface plasmon resonance analysis in accordance with the present invention, may be performed with the processing for coating a solution, which contains the physiologically active substance. The term "coating" as used herein embraces the dipping technique. In cases where the physiologically active substance has the nitrogen-containing heterocyclic ring group, the nitrogen-containing heterocyclic ring of the physiologically active substance coordinates with the metal ion to form a complex, and the physiologically active substance is there by fixed (as illustrated in FIG. 4).

In cases where the metal ion and the nitrogen-containing heterocyclic ring group of the physiologically active substance are imparted to the ligand, which has been bound with the support, (i) the ligand, (ii) the nitrogen-containing heterocyclic ring group of the physiologically active substance, and (iii) a water molecule or a hydroxide ion coordinate with the metal ion to form the complex.

For example, in cases where NTA is utilized as the ligand, and a metal ion, which is capable of having a coordination number of six, is imparted, among the six coordination sites, four coordination sites are occupied by (i) the three carboxyl groups and one nitrogen atom, which NTA has, and the two remaining coordination sites are occupied by (ii) the nitrogen-containing heterocyclic ring group of the physiologically active substance and (iii) a water molecule or a hydroxide ion, or the like. A hexacoordinate complex is thereby formed.

In cases where iminodiacetic acid is utilized as the ligand, and a metal ion, which is capable of having a coordination number of six, is imparted, among the six coordination sites, three coordination sites are occupied by (i) the two carboxyl groups and one nitrogen atom, which iminodiacetic acid has, and the three remaining coordination sites are occupied by (ii) the nitrogen-containing heterocyclic ring group of the physiologically active substance and (iii) a water molecule or a hydroxide ion, or the like. A hexacoordinate complex is thereby formed.

As in the cases described above under "(6) Fixation of physiologically active substance" for the carrier in accordance with the present invention, in the examples described above, the metal ion, which is capable of having a coordination number of six, is employed. However, the coordination number may be at least seven. Alternatively, the coordination number may be at most five. Also, the carboxyl groups for the formation of the complex need not necessarily be supplied by one piece of the ligand, and the carboxyl groups may be supplied by multiple pieces of the ligand and may thus form the complex.

The chip for surface plasmon resonance analysis in accordance with the present invention is capable of being applied to the surface plasmon resonance biosensor, which has been described above under "(8-2) Application to biosensor" for the carrier in accordance with the present invention.

The carrier in accordance with the present invention will further be illustrated by the following non-limitative examples.

EXAMPLES

Example 1

(Preparation of SAM)

A chromium film having a thickness of 3 nm and a gold film having a thickness of 20 nm were formed on a polystyrene microwell plate (96 Well Microwell Plate, supplied by Nunc) by use of a sputtering technique. Thereafter, a solution, which contained 10 µmol of 6-aminohexanethiol (supplied by Aldrich) dissolved in 8 ml of ethanol and 2 ml of ultra pure water, was allowed to undergo reaction with the gold film, which had been formed with the sputtering technique described above, at a temperature of 40° C. for one hour. The resulting SAM was then washed one time with ethanol and was thereafter washed one time with ultra pure water.

(Activating Esterification of CMD)

A CMD solution was prepared with processing wherein CMD (molecular weight: 1,000,000, supplied by Meito Sangyo Co., Ltd.) was dissolved in ultra pure water so as to have a concentration of 0.5% by weight. Thereafter, a mixed solution, which contained 0.4M of EDC (i.e., 1-(3-dimethylaminopropyl)-3-ethylcarbodiimide) and 0.1M of NHS (i.e., N-hydroxysuccinimide), was added to the CMD solution. The mixed solution was added in a stoichiometric quantity having been calculated such that, in cases where the entire quantity had undergone the reaction, 2% of the carboxyl group might be activated. The resulting reaction mixture was stirred at the room temperature for five minutes.

(Formation of CMD Film)

The CMD solution having been subjected to the activating esterification was added little by little onto the SAM having been formed on the base plate. The CMD solution was then removed after a period of time of 30 seconds. In this manner, a thin film of carboxymethyl dextran having been subjected to the activating esterification was formed on the base plate having the amino group. After being allowed to undergo the reaction at the room temperature for one hour, the thin film was washed one time with 0.1N NaOH and was then washed one time with ultra pure water.

Binding of AB-NTA
N-(5-amino-1-carboxypentyl)iminodiacetic acid)

A solution was prepared by the addition of 1 mmol of EDC and 0.2 mmol of NHS to 1 ml of DMSO, and 50 µl of the thus prepared solution was added onto the CMD film. The solution was then allowed to undergo the reaction at the room temperature for 30 minutes. After the solution was removed, washing with DMSO was performed one time. Also, a solution prepared by the addition of 0.1 mmol of AB-NTA (supplied by Dojin Kagaku K.K.) to 1 ml of DMSO was allowed to undergo the reaction for 12 hours. The solution was removed, and washing with ultra pure water was performed one time.

(Fixation of p38 MAP Kinase α)

An aqueous solution of $CuCl_2$ having a concentration of 1 mmol/l was added in a quantity sufficient with respect to the number of pieces of AB-NTA having been bound on the base plate. The solution was removed after a period of time of three minutes, and washing with ultra pure water was performed two times. Thereafter, a sufficient quantity of 2.5 ug/ml His6-p38 MAP Kinase α (supplied by CALBIOCHEM) was added. The solution was removed after a period of time of 15 minutes, and washing was performed with a 200 µM aqueous imidazole solution.

Example 2

A carrier was prepared in the same manner as that in Example 1, except that, at the time of the binding of AB-NTA, a solution was prepared by the addition of 0.2 mmol of EDC and 0.04 mmol of NHS to 1 ml of DMSO, 50 µl of the thus prepared solution was added onto the CMD film, and the solution was then allowed to undergo the reaction at the room temperature for 30 minutes.

Examples 3, 4, and 5

A carrier was prepared in the same manner as that in Example 1, except that the kind of the metal source was changed as listed in Table 1 below.

Example 6

A carrier was prepared in the same manner as that in Example 1, except that, at the time of the binding of AB-NTA, in lieu of DMSO, DMF was utilized as the reaction solvent.

Example 7

A carrier was prepared in the same manner as that in Example I, except that, at the time of the binding of AB-NTA, a mixed solution, which contained 2M of EDC and 0.5M of NHS, was used in lieu of 1 mmol of EDC and 0.2 mmol of NHS being used, and a solution, which contained 0.1 mmol of AB-NTA, 0.06 ml of DBU (supplied by Tokyo Chemical Industry Co., Ltd.), and 0.94 ml of DMSO, was added in lieu of the solution prepared by the addition of 0.1 mmol of AB-NTA to 1 ml of DMSO being used.

Example 8

A carrier was prepared in the same manner as that in Example I, except that, at the time of the binding of AB-NTA, a solution containing 0.1 mmol of AB-NTA, 0.06 ml of DBU, and 0.94 ml of DMSO was added in lieu of the solution prepared by the addition of 0.1 mmol of AB-NTA to 1 ml of DMSO being used.

Comparative Example 1

A carrier was prepared in the same manner as that in Example 5, except that, at the time of the binding of AB-NTA, $H_2O$ was used in lieu of DMSO being used.

Comparative Example 2

A carrier was prepared in the same manner as that in Example 1, except that, at the time of the binding of AB-NTA, $H_2O$ was used in lieu of DMSO being used.
(Ligand Density)

At the stage after the binding of AB-NTA had been performed during the preparation of each of the carriers in Examples 1 to 8 and Comparative Examples 1 and 2, an aqueous solution of $NiCl_2$ having a concentration of 0.1 mol/l was added. The solution was removed after a period of time of 10 minutes, and washing with ultra pure water was performed two times. Thereafter, extraction with 5 ml of an aqueous 50 mM EDTA solution was performed two times. The extraction liquids obtained from the two times of the extraction were combined together and subjected to the measurement with an ICP analysis apparatus and the detection of the Ni number. The number of pieces of the ligand was calculated from the Ni number and the well bottom area (38 $mm^2$), and the ligand density was thereby calculated.
(Specific Activity of p38 MAP Kinase α)

After each of the carriers in Examples 1 to 8 and Comparative Examples 1 and 2 had been prepared, 1 µl of 1 mM $MgCl_2$, 0.6 µl of 1 mM ATP, 35 µl of 0.27M Myelin Basic Protein, and 13 µl of TBS buffer were added to the carrier and allowed to undergo the reaction at the room temperature for one hour. Thereafter, the solution was recovered, and 50 µl of Kinase-Glo (supplied by Promega) was added. After the liquid had been allowed to stand at the room temperature for 10 minutes, measurement of light emission intensity was made with LAS-3000 (supplied by Fuji Photo Film Co., Ltd.). For the evaluation of the specific activity, the thus measured light emission intensity was represented as a relative value with the light emission intensity, which was obtained for the carrier of Comparative Example 2, being taken as 1.

The results shown in Table 1 below were obtained.

TABLE 1

| | AB-NTA reaction liquid | | | Ligand density | Specific activity of |
|---|---|---|---|---|---|
| | Solvent | Concentration (mol/l) | Metal source | (pieces/$mm^3$) | p38 MAP Kinase α |
| Example 1 | DMSO | 0.1 | $CuCl_2$ | $3.6 \times 10^{16}$ | 25 |
| Example 2 | DMSO | 0.01 | $CuCl_2$ | $1.4 \times 10^{16}$ | 16 |
| Example 3 | DMSO | 0.1 | $CoCl_2$ | $4.2 \times 10^{16}$ | 12 |
| Example 4 | DMSO | 0.1 | $FeCl_2$ | $3.7 \times 10^{16}$ | 8 |
| Example 5 | DMSO | 0.1 | $NiCl_2$ | $3.5 \times 10^{16}$ | 19 |
| Example 6 | DMF | 0.01 | $CuCl_2$ | $1.0 \times 10^{16}$ | 14 |
| Example 7 | DMSO | 0.1 | $CuCl_2$ | $1.8 \times 10^{17}$ | 32 |
| Example 8 | DMSO | 0.1 | $CuCl_2$ | $5.7 \times 10^{16}$ | 27 |
| Comp. Ex. 1 | $H_2O$ | 0.1 | $NiCl_2$ | $7.8 \times 10^{15}$ | 1.3 |
| Comp. Ex. 2 | $H_2O$ | 0.1 | $CuCl_2$ | $7.0 \times 10^{15}$ | 1 |

As clear from Table 1, as for each of the carriers having been prepared in Examples 1 to 8, in which the organic solvent was used as the reaction liquid at the time of the binding of AB-NTA, the ligand density was high, and p38 MAP Kinase a was fixed reliably with His-tag as clear from the specific activity of p38 MAP Kinase α.

In Example 7, the concentrations of EDC and NHS used at the time of the activation of CMD were set to be higher than in Example 1, and DBU was used as the additive at the time of the binding of AB-NTA acting as the ligand in Example 1. Also, in Example 8, DBU was used as the additive at the time of the binding of AB-NTA in Example 1. As for each of the carriers having been prepared in Examples 7 and 8, the ligand density and the specific activity of p38 MAP Kinase α were higher than those in the carrier having been prepared in Example 1. It was thus been found that the utilization of the base as the additive was efficient for enhancing the ligand binding rate.

The chip for surface plasmon resonance analysis in accordance with the present invention will further be illustrated by the following non-limitative examples.

Example 9

(Preparation of Base Plate Having Amino Group)

After Sensor Chip Au (supplied by Biacore) constituted of a sensor chip, on which only a gold film had been formed, was subjected to UV ozone processing for 12 minutes, a solution, which contained 10 µmol of 6-aminohexanethiol (supplied by Aldrich) dissolved in 8 ml of ethanol and 2 ml of ultra pure water, was allowed to undergo reaction with the gold film at a temperature of 40° C. for one hour. An amino group was thus formed on the gold film. The base plate having the amino group was then washed one time with ethanol and was thereafter washed one time with ultra pure water.
(Activating Esterification of CMD)

A CMD solution was prepared with processing wherein CMD (molecular weight: 1000,000, supplied by Meito Sangyo Co., Ltd.) was dissolved in ultra pure water so as to have a concentration of 0.5% by weight. Thereafter, a mixed solution, which contained 0.4M of EDC (i.e., 1-(3-dimethylaminopropyl)-3-ethylcarbodiimide) and 0.1M of NHS (i.e., N-hydroxysuccinimide), was added to the CMD solution. The mixed solution was added in a stoichiometric quantity having been calculated such that, in cases where the entire quantity had undergone the reaction, 2% of the carboxyl group might be activated. The resulting reaction mixture was stirred at the room temperature for five minutes.

(Preparation of CMD Film)

The CMD solution having been subjected to the activating esterification was added little by little onto the gold film, on which the amino group had been formed. The CMD solution was then removed after a period of time of 30 seconds. In this manner, a thin film of carboxymethyl dextran having been subjected to the activating esterification was formed on the base plate having the amino group. After being allowed to undergo the reaction at the room temperature for one hour, the thin film was washed one time with 0.1N NaOH and was then washed one time with ultra pure water.

Preparation of AB-NTA
(N-(5-amino-1-carboxypentyl)iminodiacetic acid)
Film

A solution was prepared by the addition of 1 mmol of EDC and 0.2 mmol of NHS to 1 ml of DMSO, and 50 µl of the thus prepared solution was added onto the CMD film. The solution was then allowed to undergo the reaction at the room temperature for 30 minutes. After the solution was removed, washing with DMSO was performed one time. Also, a solution prepared by the addition of 0.1 mmol of AB-NTA (supplied by Dojin Kagaku K.K.) to 1 ml of DMSO was allowed to undergo the reaction for 12 hours. The solution was removed, and washing with ultra pure water was performed one time.

(Fixation of Protein)

The sample having been prepared was set on a surface plasmon resonance apparatus (Biacore3000, supplied by Biacore). After an SPR HEPES buffer (20 mM HEPES-HCl, 150 mM NaCl, pH7.2) was stabilized at a flow rate of 10 µl/min, 10 µl of an aqueous $NiCl_2$ solution having a concentration of 1 mmol/l was added. Thereafter, washing with 20 µl of an HBS-N buffer was performed one time. Thereafter, 10 µl of an aqueous solution of His10-Ubi (ubiquitin having been bound with a linkage of 10 histidine units) having a concentration of 1 µmol/l was added. In this manner, a chip for surface plasmon resonance analysis was prepared.

Example 10

A chip for surface plasmon resonance analysis was prepared in the same manner as that in Example 9, except that $CuCl_2$ was used in lieu of $NiCl_2$ acting as the metal ion source utilized in the fixation of the protein in Example 9, and except that, at the time of the binding of AB-NTA, a solution was prepared by the addition of 0.2 mmol of EDC and 0.04 mmol of NHS to 1 ml of DMSO, 50 µl of the thus prepared solution was added onto the CMD film, and the solution was then allowed to undergo the reaction at the room temperature for 30 minutes.

Example 11

A chip for surface plasmon resonance analysis was prepared in the same manner as that in Example 9, except that $CuCl_2$ was used in lieu of $NiCl_2$ acting as the metal ion source utilized in the fixation of the protein in Example 9, except that, at the time of the activation of CMD, a mixed solution, which contained 2M of EDC and 0.5M of NHS, was added, and except that, at the time of the binding of AB-NTA, a solution, which contained 0.1 mmol of AB-NTA, 0.06 ml of DSU (supplied by Tokyo Chemical Industry Co., Ltd.), and 0.94 ml of DMSO, was added in lieu of the solution prepared by the addition of 0.1 mmol of AB-NTA (supplied by Dojin Kagaku K.K.) to 1 ml of DMSO being used.

Comparative Example 3

A chip for surface plasmon resonance analysis was prepared in the same manner as that in Example 9, except that His6-Ubi (ubiquitin having been bound with a linkage of six histidine units) was used in lieu of His10-Ubi (ubiquitin having been bound with a linkage of 10 histidine units) utilized in the fixation of the protein in Example 9.

Comparative Example 4

A chip for surface plasmon resonance analysis was prepared in the same manner as that in Example 9, except that, at the time of the binding of AB-NTA in Example 9, a solution was prepared by the addition of 0.2 mmol of EDC and 0.04 mmol of NHS to 1 ml of DMSO, 50 µl of the thus prepared solution was added onto the CMD film, and a liquid having an AB-NTA concentration of 10 mM was allowed to undergo the reaction at the room temperature for 30 minutes.

(Ligand Density)

At the stage after the binding of AB-NTA had been performed during the preparation of each of the chips for surface plasmon resonance analysis in Examples 9 to 11 and Comparative Examples 3 and 4, an aqueous solution of $NiCl_2$ having a concentration of 0.1M was added. The solution was removed after a period of time of 10 minutes, and washing with ultra pure water was performed two times. Thereafter, extraction with 5 ml of an aqueous 50 mM EDTA solution was performed two times. The extraction liquids obtained from the two times of the extraction were combined together and subjected to the measurement with an TOP analysis apparatus and the detection of the Ni number. The number of pieces of the ligand was calculated from the Ni number and the well bottom area (38 $mm^2$), and the ligand density was thereby calculated.

(Measurement of Protein Fixation Rate)

Alteration of a protein dissociation quantity with the passage of time at the stage immediately after the protein fixation was performed and at the stage of flowing of a buffer for 10 minutes was measured by use of Biacore3000. The protein fixation rate was calculated from the protein fixation quantity at the stage immediately after the protein fixation was performed and the protein fixation quantity at the stage after the passage of time of 10 minutes.

The results as shown in Table 2 and FIG. 5 were obtained. FIG. 5 is a graph showing alterations of a protein fixation quantity (a protein fixation rate) with the passage of time of 10 minutes from the stage immediately after the protein fixation was performed, which alterations were found for the chips for surface plasmon resonance analysis having been prepared in Example 9 and Comparative Example 3.

TABLE 2

|  | Ligand density (pieces/mm³) | Metal source | Protein | Fixation rate |
|---|---|---|---|---|
| Example 9 | $3.6 \times 10^{16}$ | $NiCl_2$ | His10-Ubi | 0.96 |
| Example 10 | $1.0 \times 10^{16}$ | $CuCl_2$ | His10-Ubi | 0.99 |
| Example 11 | $1.8 \times 10^{17}$ | $CuCl_2$ | His10-Ubi | 0.99 |
| Comp. Ex. 3 | $3.7 \times 10^{16}$ | $NiCl_2$ | His6-Ubi | 0.26 |
| Comp. Ex. 4 | $0.9 \times 10^{16}$ | $NiCl_2$ | His10-Ubi | 0.19 |

As clear from Table 2, as for each of the chips for surface plasmon resonance analysis having been prepared in Comparative Examples 3 and 4, the protein fixation rate, i.e. the protein retaining capability with the passage of time of 10 minutes, was low. As for each of the chips for surface plasmon resonance analysis having been prepared in Examples 9, 10, and 11, in which the ligand density was high, and in which the number of the histidine units was equal to 10, the protein fixation rate was high. In cases where the protein fixation rate was high, the interaction with the sample substance was capable of being detected reliably, and the detection sensitivity was capable of being kept high.

Example 12

The steps up to the preparation of the CMD film were performed in the same manner as that in Example 9, and the subsequent steps were altered to those described below.

(Preparation of AB-NTA Film)

A solution was prepared by the addition of 1 mmol of EDC and 0.2 mmol of NHS to 1 ml of DMSO, and 50 µl of the thus prepared solution was added onto the CMD film. The solution was then allowed to undergo the reaction at the room temperature for 30 minutes. After the solution was removed, washing with DMSO was performed one time. Also, a solution, which contained 0.1 mmol of AB-NTA (supplied by Dojin Kagaku K.K.), 0.06 ml of DEU (supplied by Tokyo Chemical Industry Co., Ltd.), and 0.94 ml of DMSO, was added to 1 ml of DMSO, and the thus prepared solution was allowed to undergo the reaction for 2 hours. The solution was removed, and washing with ultra pure water was performed one time.

(Fixation of Peptide)

The sample having been prepared was set on a surface plasmon resonance apparatus (Biacore3000, supplied by Biacore). After an SPR HEPES buffer (20 mM HEPES-HCl, 150 mM NaCl, pH7.2) was stabilized at a flow rate of 10 µl/min, 10 µl of an aqueous $CuCl_2$ solution having a concentration of 1 mmol/l was added. Thereafter, washing with 20 µl of an HBS-N buffer was performed one time. Thereafter, 5 µl of an aqueous solution of His-His-His-His-Glycine-Serine-His-His-His-His (supplied by Operon) having a concentration of 5 µmol/l was added. In this manner, a chip for surface plasmon resonance analysis was prepared.

Comparative Example 5

A chip for surface plasmon resonance analysis was prepared in the same manner as that in Example 12, except that an aqueous solution of His-His-His-Glycine-Serine-Glycine-Serine-His-His-His (supplied by Operon) was used in lieu of the aqueous solution of His-His-His-His-Glycine-Serine-His-His-His-His (supplied by Operon) utilized in the fixation of the peptide in Example 12.

(Ligand Density)

The ligand density was calculated in the same manner as that in Examples 9, 10, 11 and Comparative Examples 3 and 4.

(Measurement of Peptide Fixation Rate)

Alteration of a peptide dissociation quantity with the passage of time at the stage immediately after the peptide fixation was performed and at the stage of flowing of a buffer for six hours was measured by use of Biacore3000. The peptide fixation rate was calculated from the peptide fixation quantity at the stage immediately after the peptide fixation was performed and the peptide fixation quantity at the stage after the passage of time of six hours.

The results as shown in Table 3 were obtained.

TABLE 3

|  | Ligand density (pieces/mm³) | Metal source | Peptide | Fixation rate |
|---|---|---|---|---|
| Example 12 | $4.5 \times 10^{16}$ | $CuCl_2$ | His-His-His-His-Gly-Ser-His-His-His-His | 0.93 |
| Comp. Ex. 5 | $4.5 \times 10^{16}$ | $CuCl_2$ | His-His-His-Gly-Ser-Gly-Ser-His-His-His | 0.83 |

As clear from Table 3, the chip for surface plasmon resonance analysis having been prepared in Example 12, in which the number of the histidine units was equal to eight, exhibited the peptide fixation rate, i.e. the peptide retaining capability with the passage of time of six hours, which was higher than the peptide fixation rate obtained with the chip for surface plasmon resonance analysis having been prepared in Comparative Example 5, in which the number of the histidine units was equal to six. In cases where the peptide fixation rate was high, the interaction with the sample substance was capable of being detected reliably, and the detection sensitivity was capable of being kept high. Also, it was found that in cases where the histidine units were not continuous, it was possible to achieve the fixation.

What is claimed is:

1. A process for producing a carrier comprising a base plate, a polymeric film formed on the base plate, and a chelating agent bound to the polymeric film, said process comprising steps of:
    forming the polymeric film that includes a thin hydrophilic film constituted by a hydrophilic polymer, the hydrophilic polymer having a molecular weight within a range from 10000 to 2000000, on the base plate by reacting the hydrophilic polymer with the base plate in the state of a thin film; and
    reacting the chelating agent and a base additive with the thin hydrophilic film in an organic solvent in order to cause the chelating agent to bind to the polymeric film,
    wherein said chelating agent is one or more selected from the group consisting of a nitrilotriacetic acid compound, iminodiacetic acid compound phenanthroline compound, terpyridine compound, bipyridine compound, triethylenetetramine compound, diethylenetriamine compound, tris(carboxymethyl)ethylenediamine compound, diethylenetriaminepentaacetic acid compound, polypyrazolylboric acid compound, 1,4,7-triazocyclononane compound, and dimethylglyoxime compound.

2. A process for producing a carrier as defined in claim 1, wherein:
    the base additive is 1,8-diazabicyclo[5.4.0]undec-7-ene.

3. A process for producing a carrier as defined in claim 1, wherein:
    the organic solvent is one of dimethyl sulfoxide and N,N-dimethylformamide.

4. A process for producing a carrier as defined in claim 3, wherein:
the organic solvent is dimethyl sulfoxide.

5. A process for producing a carrier as defined in claim 1, wherein the chelating agent is bound to the polymeric film via activated carboxyl groups of the polymeric film.

6. A process for producing a carrier as defined in claim 1, wherein:
the polymeric film formed by the reaction of the hydrophilic polymer and the base plate further contains a self assembling monolayer,
wherein the thin hydrophilic film constituted by a hydrophilic polymer is formed on the self assembling monolayer, and the chelating agent is bound to the thin hydrophilic polymer film.

7. A process for producing a carrier as defined in claim 1, wherein:
the method for causing the hydrophilic polymer to react with the base plate in the state of a thin film is one selected from the group consisting of an extrusion coating technique, a curtain coating technique, a casting technique, a screen printing technique, a spin coating technique, a spray coating technique, a slide beads coating technique, a slit and spin technique, a slit coating technique, a die coating technique, a dip coating technique, a knife coating technique, a blade coating technique, a flow coating technique, a roll coating technique, a wire bar boating technique, and a transfer printing technique.

* * * * *